(12) United States Patent
Campbell et al.

(10) Patent No.: US 9,644,940 B2
(45) Date of Patent: May 9, 2017

(54) SYSTEM AND METHOD FOR SENSING AMMONIA

(71) Applicant: Lumense, Inc., Atlanta, GA (US)

(72) Inventors: Daniel Campbell, Atlanta, GA (US); Jayme Caspall, Decatur, GA (US); Janet Cobb-Sullivan, Marietta, GA (US); Bonnie Bobzin, Mableton, GA (US); Kenneth Johnson, Kennesaw, GA (US); Robert E. Jones, Atlanta, GA (US); Michael Slawson, Atlanta, GA (US)

(73) Assignee: Lumense, Inc., Norcross, GA (US)

( * ) Notice: Subject to any disclaimer, the term of this patent is extended or adjusted under 35 U.S.C. 154(b) by 523 days.

(21) Appl. No.: 14/153,456

(22) Filed: Jan. 13, 2014

(65) Prior Publication Data

US 2014/0311350 A1    Oct. 23, 2014

Related U.S. Application Data

(60) Provisional application No. 61/751,430, filed on Jan. 11, 2013.

(51) Int. Cl.
| | |
|---|---|
| *G01B 9/02* | (2006.01) |
| *G01N 33/00* | (2006.01) |
| *B01D 29/60* | (2006.01) |
| *B01D 46/46* | (2006.01) |
| *G01N 21/77* | (2006.01) |
| *G01N 21/85* | (2006.01) |

(Continued)

(52) U.S. Cl.
CPC .......... *G01B 9/02015* (2013.01); *A01K 31/00* (2013.01); *B01D 29/60* (2013.01); *B01D 46/46* (2013.01); *G01N 21/7703* (2013.01); *G01N 21/85* (2013.01); *G01N 33/0054* (2013.01); *G01N 33/0063* (2013.01); *G01N 2021/458* (2013.01); *G01N 2021/7779* (2013.01)

(58) Field of Classification Search
CPC ................. G01B 9/02; G01N 33/1826; G01N 2021/7779; G01N 33/0054; B01D 29/60; B01D 46/44
See application file for complete search history.

(56) References Cited

U.S. PATENT DOCUMENTS

| | | | | |
|---|---|---|---|---|
| 8,284,403 B2* | 10/2012 | Carson | ................... | G01N 21/33 356/437 |
| 2002/0016005 A1* | 2/2002 | Campbell | .............. | G01N 21/41 436/100 |

(Continued)

*Primary Examiner* — Kara E Geisel
*Assistant Examiner* — Maurice Smith
(74) *Attorney, Agent, or Firm* — Smith, Gambrell & Russell

(57) ABSTRACT

A system and method for the monitoring of ammonia in a fluid. The ammonia monitoring system includes an ammonia sensor that is configured to detect trace amounts of ammonia ($NH_3$) in a fluid (i.e., gas or liquid) that is pumped through it in real time. The real time ammonia sensor includes an interferometer configured to track the amount of ammonia that is pumped into the real time ammonia sensor. The ammonia monitoring system, via the real time ammonia sensor, is further configured to detect ammonia levels in industrial poultry houses and provide electronic feedback to the building's ventilation control system.

7 Claims, 13 Drawing Sheets

(51) Int. Cl.
*A01K 31/00* (2006.01)
*G01N 21/45* (2006.01)

(56) References Cited

U.S. PATENT DOCUMENTS

| | | | |
|---|---|---|---|
| 2003/0166294 A1* | 9/2003 | Kirby | G01N 21/3504 436/134 |
| 2005/0068543 A1* | 3/2005 | Angeley | G01N 21/4788 356/521 |
| 2005/0122572 A1* | 6/2005 | Campbell | B01D 39/1623 359/337.22 |
| 2009/0032011 A1* | 2/2009 | Livchak | F24C 15/20 126/299 D |
| 2010/0271634 A1* | 10/2010 | Dominguez Horna | G01N 21/45 356/477 |
| 2011/0292398 A1* | 12/2011 | Klein Koerkamp | G01N 21/7703 356/477 |
| 2012/0214707 A1* | 8/2012 | Ymeti | G01N 21/45 506/9 |

* cited by examiner

SYSTEM AND METHOD FOR SENSING AMMONIA

CLAIM OF PRIORITY

This application claims priority from U.S. Provisional Patent Application 61/751,430, filed Jan. 11, 2013, which is relied upon and incorporated herein in its entirety by reference.

BACKGROUND

Ammonia is a byproduct of poultry excretion. Studies have shown that maintenance of low ammonia levels in industrial poultry houses is an important factor in increasing processing yield and feed efficiency, reducing bird stress and disease, and improving bird uniformity. Birds subject to high levels of ammonia weigh less, on average, than birds growing in low levels. Additionally, there is a greater spread in bird weight, and greater numbers of significantly undersized birds, making processing more difficult. High ammonia levels also negatively affect bird welfare at minimum and major levels. Levels above 35 parts per million (ppm) may adversely affect birds' growth, respiration, and disease immunity over time. At ammonia levels above 50 ppm, the spread of viruses, like Newcastle disease virus, can accelerate exponentially in a flock to the point where the whole flock can be lost. Conical lesions also dramatically increase at ammonia levels above 50 ppm. Above 100 ppm, birds may face immediate life threatening danger if action is not taken.

In order to control the amount of ammonia exposure, industrial poultry houses are ventilated based upon the levels of ammonia found in such poultry houses. However, humans vary in their ability to smell ammonia at levels below 50 ppm. Ammonia is currently managed by taking occasional point measurements using disposable colormatic tubes, and/or by tracking poultry house humidity as a loose proxy for ammonia, and then trying to set ventilation regimens accordingly. Such a process is burdensome, since it requires constant manual monitoring and adjustment. Further, ventilation can quickly become ineffective, particularly at nighttime. The building's lighting, ventilation, heating, humidity, and other parameters are typically adjusted automatically by a controller. The controller generally reduces ammonia levels by increasing ventilation, but excessive ventilation can reduce temperature inside the building, also negatively impacting bird health and increasing energy costs.

Therefore, there is a need for a real-time continuous ammonia sensor that can be used to continuously optimize ventilation. Further, there is a need for the real-time ammonia sensor to function in an automated feedback loop that keeps ammonia levels in the desired range using minimum ventilation.

SUMMARY OF INVENTION

The present invention provides an ammonia monitoring system. The ammonia monitoring system includes an ammonia sensor that is configured to detect trace amounts of ammonia ($NH_3$) in a fluid (i.e., gas or liquid) that is pumped through it in real time. The real time ammonia sensor includes an interferometer configured to track the amount of ammonia that is pumped into the real time ammonia sensor. The ammonia monitoring system, via the real time ammonia sensor, is further configured to detect ammonia levels in industrial poultry houses and provide electronic feedback to the building's ventilation control system.

In one embodiment of the present invention, the ammonia monitoring system is further configured to display ammonia levels determined by the real time ammonia sensor in real time.

According to another embodiment of the present invention, the ammonia monitoring system is configured to log historical data, including data related to the ammonia levels detected by the real time ammonia sensor.

According to another embodiment of the present invention, the real time ammonia monitoring system is further configured to issue threshold alerts.

These and other objects and advantages of the invention will become apparent from the following detailed description of the preferred embodiment of the invention.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DETAILED DESCRIPTION OF THE PREFERRED EMBODIMENTS

Figure 1:
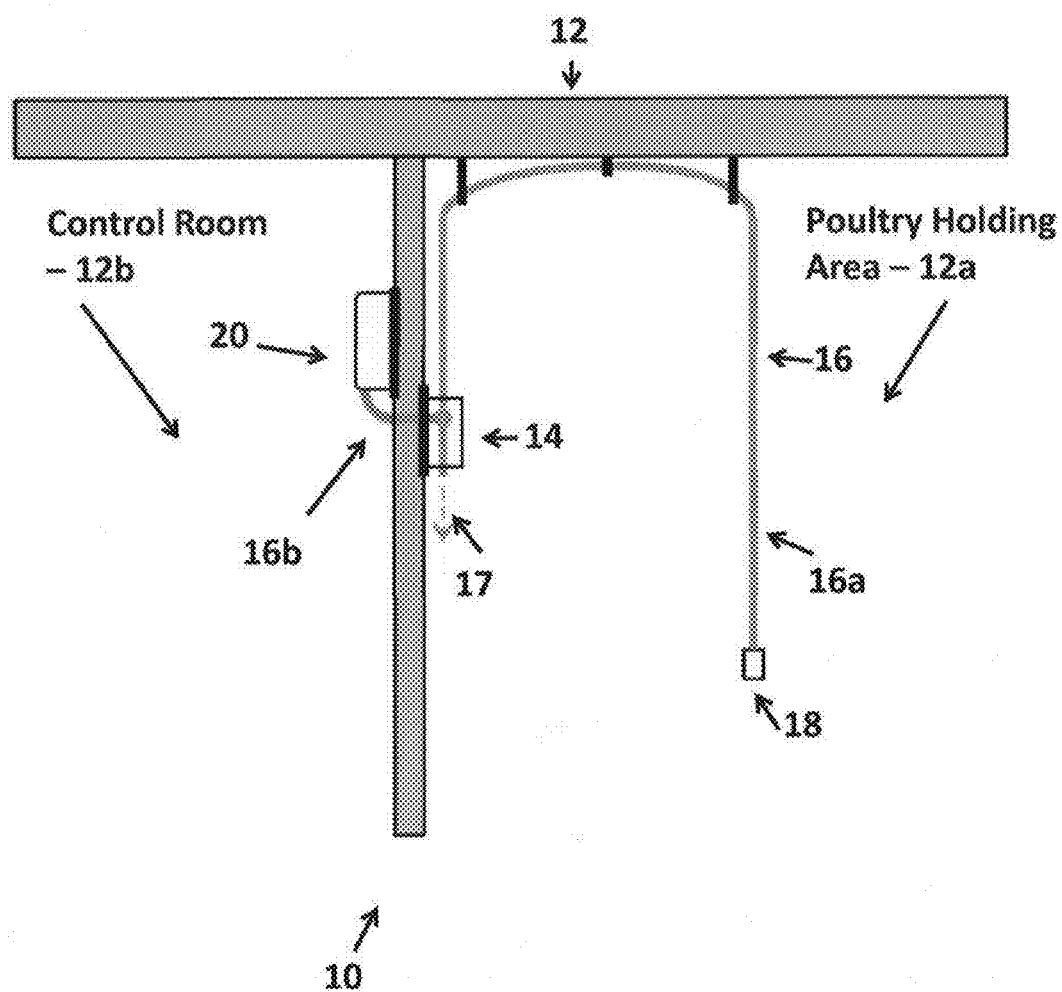
FIG. 1 is a schematic representation of an ammonia monitoring system according to one embodiment.

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer readable memory that can direct a computer or other programmable data processing apparatus to function in a particular manner, such that the instructions stored in the computer-readable memory produce an article of manufacture including computer readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions, and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Figure 2:
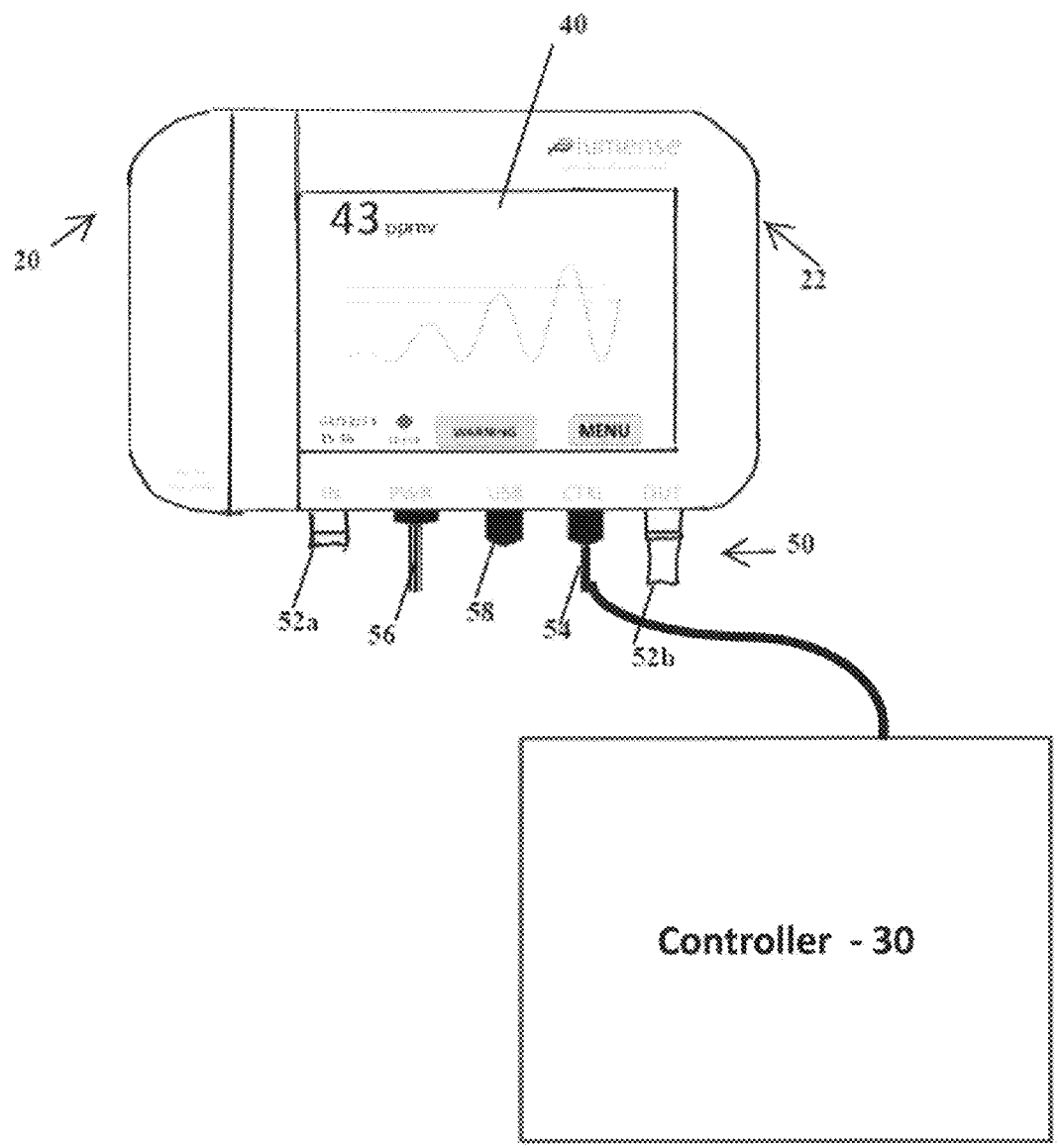
FIG. 2 is a schematic representation of components of the ammonia monitoring system of FIG. 1.
Figure 3:
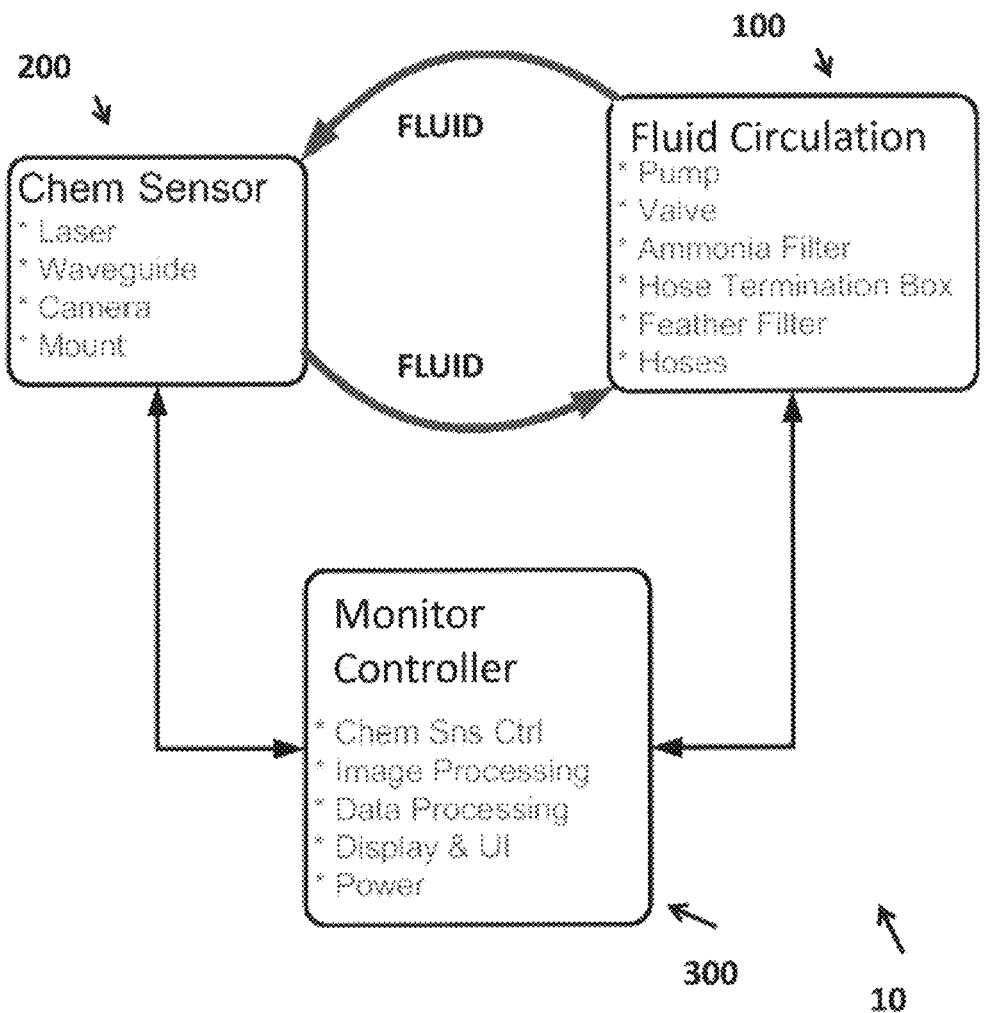
FIG. 3 is a relational diagram of the subsystems of the ammonia monitoring system of FIG. 1.

Referring to FIGS. 1-2, the present invention is directed to an ammonia monitoring system 10. In an exemplary aspect, the ammonia monitoring system 10 illustrated in FIGS. 1-2 is configured for use in poultry houses 12. While FIGS. 1-2 show the ammonia monitoring system 10 configured for monitoring air in poultry houses 12, the ammonia monitoring system 10 can be used in a variety of settings in which the continuous monitoring for ammonia in a fluid (i.e., gas or liquid) is needed. For example, the ammonia monitoring system 10 can be configured for use in concentrated animal feed operations, such as, but not limited to, turkey grow-out and swine houses. Further, the ammonia monitoring system 10 can be utilized in utility industry settings. Such industrial settings include, but are limited to, remediating dangerous smokestack gases with ammonia and the monitoring of ammonia leaks when ammonia is utilized as a coolant. In addition, components of the ammonia monitoring system 10 as described below can be modified for use in environmental protection applications, including, but not limited to, measuring the ammonia level in water.

The ammonia monitoring system 10 includes a real time ammonia sensor 20, a junction box 14, intake hoses 16 and exhaust hoses 17, and a dust and feather filter 18. Further, the ammonia monitoring system 10, and more specifically, the real time ammonia sensor 20, are configured to interact with the house controller 30 (see FIG. 2) of the poultry house 12, and more specifically, with the ventilation components of the control system, including the house controller 30, of the poultry house 12.

In an aspect, the ammonia monitoring system 10 is configured for use in a poultry house 12, with the junction box 14, intake hoses 16, exhaust hoses 17, and dust and feather filter 18 configured to be located within the poultry holding area 12a, and the real time ammonia sensor 20 located in the control room 12b. In some aspects, the ammonia monitoring system 10 can also include additional in-house sensors (not shown) positioned within the poultry holding area 12a. Such sensors can include, but are not limited to, humidity and temperature sensors, and can be found in the junction box 14. Various fastening means, including, but not limited to, mounting brackets, may be used to secure the components of the ammonia monitoring system 10 at their respective positions within the poultry house 12. While the junction box 14 and the real time ammonia sensor 20 can be mounted at various locations within the poultry holding area 12a and the control room 12b respectively, it is preferable that the junction box 14 and real time ammonia sensor 20 be mounted approximate to one another on a shared wall. For example, it is preferable to mount the real time ammonia sensor 20 approximately five feet off the ground to facilitate touchscreen operation with the junction box 14 mounted at a level about a foot below the bottom of the sensor. While the above describes the preferred mounting configuration, the ammonia monitoring system 10 is not limited to such. For example, other embodiments of the ammonia monitoring system 10 include having the ammonia sensor 20 and junction box 14 within the poultry house itself. Further, in some settings, the ammonia monitoring system 10 may not require a junction box 14. All that is needed is for the ammonia monitoring system 10 to have ways to provide fluid from a poultry holding area 12a to the real time ammonia sensor 20.

In an aspect, the junction box 14 provides a protected location to house the junctions and cover holes drilled in the wall for the intake hoses 16 and exhaust hoses 17 to connect to the real time ammonia sensor 20. In an aspect, the junction box 14 includes a mounting flange and is of sturdy enough construction to withstand pressure washing during house cleanout of the industrial poultry house 12 (and more specifically, the poultry holding area 12a) between flocks. In an aspect, the junction box 14 has two air paths, one for the poultry house intake hose 16 and one for the exhaust hose 17, both discussed in more detail below. In an aspect, the junction box 14 preferably includes a cover that is removable during end-of-cycle maintenance.

In an exemplary aspect of the invention, the intake hose 16 of the ammonia monitoring system 10 can be configured to be comprised of two sections, one section 16b for use in the control room side 12b and one section 16a for use in the poultry holding area 12a. In an exemplary aspect, both sections 16a, 16b of the intake hose 16 are of a standard size. In an exemplary aspect, the diameter of the sections 16a, 16b can be ¼ inch. Hoses 16a, 16b with larger diameters can require longer priming time as well as increased surface area for condensation, which can lead to a less efficient ammonia monitoring system 10. However, the sections 16a, 16b can have diameters of various sizes. In addition, it is preferable that the material of the intake hose 16, including the different sections 16a, 16b, are made out of a material that does not absorb ammonia and is low in surface energy to prevent moisture adhesion. In an aspect, the intake hose 16 can be made out of materials including, but not limited to, polytetrafluoroethylene (PTFE). While PTFE can absorb ammonia, it is inert and does not change ammonia chemically. The lengths of the section 16a of the intake hose 16 found in poultry holding area 12a and the section 16b of the intake hose found in the control room 12b can vary based upon the needs of the poultry house 12. In an exemplary aspect, the ammonia monitoring system 10 can be distributed a 20-50 ft section 16a of the intake hose 16 for the poultry holding area 12a and with a 2 ft section 16b of intake hose 16 for the control room side 12b. However, in other aspects, each section 16a, 16b of the intake hose 16 can be shortened as required for the particular installation. The section 16b of the intake hose 16 on the control room side 12b is configured to connect to section 16a of the intake hose 16 found in the poultry holding area 12a through the junction box 14 via a hole in the control room wall. The other end of the section 16b of the intake hose 16 found in the control room 12b is further configured to connect to the real time ammonia sensor 20 of the system 10, as shown in FIG. 1. The section 16a of the intake hose 16 stretching through the poultry holding area 12a connects to the short intake hose section 16b through the intake path of the junction box 14.

In an exemplary aspect, the sections 16a, 16b of the intake hose 16 are configured to be transparent to allow inspection for moisture, excessive dust, or debris in the intake hose 16. However, in other embodiments, the intake hose 16 may be opaque. In an aspect, one end of the section 16a of the intake hose 16 in the poultry holding area 12a can configured to be connected with the dust and feather filter 18. While the height of the end of the section 16a of the intake hose 16, and the coupled dust and feather filter 18, as placed within the poultry holding area 12a can vary. In an exemplary aspect, the end of the section 16a of the intake hose 16 is oriented so that it takes in air at a level just above the height of a full-grown chicken. In an aspect, the intake hose 16 and dust and feather filter 18 are configured to be moveable (e.g., flexible and removable) so as not to impede workers and their equipment during house maintenance.

In an aspect, the dust and feather filter 18 is configured to block objects and dust, but must not reduce the filtered fluid's humidity or affect the ammonia level in the air. The dust and feather filter 18 can be configured out of suitable materials that prevent dust particles, feather, and bugs from entering the intake hose 16. In an aspect, the ammonia monitoring system 10 can utilize a dust and feather filter 18 comprised of reticulated foam (e.g., INOAC's EZ-Dri polyether-polyurethanane foam) and a fine mesh wire screen. Filter types known to those of ordinary skill in the art can be utilized in other embodiments of the present invention.

As illustrated in FIG. 1, the ammonia monitoring system 10 includes an exhaust hose 17. While the exhaust hose 17 can be of any length, the exhaust hose 17 does not need to be extremely long because the exhaust hose 17 is used to return air to the poultry house. Further, while the diameter of the exhaust hose 17 may be of any size, it is preferable that the exhaust hose 17 diameter be of a different diameter than the section 16b of the intake hose in the control room 12b to preclude cross connection with the ammonia sensor 20. Further, it is preferable that the exhaust hose 17 include an exhaust filter 19 to prevent backflow of dust when the ammonia monitoring system 10 is not circulating air. In an aspect, the exhaust filter 19 can be changed or cleaned with water or forced air.

As shown in FIG. 2, the real time ammonia sensor 20 includes a housing 22, a user interface 40, and external connections 50. In addition, the housing 22 of the real time ammonia sensor 20 contains various hardware and software components discussed in further detail below. In an aspect, the housing 22 is configured to be rugged, and made of a sturdy material, including but not limited to, sheet metal or molded plastic, sufficient to protect the inner components of the ammonia sensor 20 and meet various safety and regulatory requirements. In an aspect, the housing 22 can include a removable filter cover, giving access to certain components of the ammonia sensor 20, including an ammonia filter cartridge, discussed in more detail below. In the preferred embodiment of the present invention, the housing 22 is configured to notify (e.g., via a switch) the various hardware and software components of the ammonia sensor 20 when the filter cover is removed or reinstalled.

In an aspect, the real time ammonia sensor 20 includes a user interface 40. In an exemplary aspect, the user interface 40 comprises a single, large, backlit color touchscreen on which all user controls and displays reside. In such an aspect, the user interface 40 can include an interactive touchscreen. While the preferred embodiment of the present invention uses an interactive touchscreen, the ammonia sensor 20 can include other types of user interfaces 40, including, but not limited to, a combination keypad and display screen, and the like. In some embodiments of the present invention, it may be desirable for the ammonia sensor 20 not to have any direct human assessable interface, limiting the control of the ammonia sensor 20 to authorized individuals remotely through a wireless or wired connection, discussed in more detail below. Specific controls and displays, and their functions, are discussed in more detail below. While the dimensions of the user interface 40 and the housing 22 can be of various combinations, it is preferable that the touchscreen display 40 be approximately 6"×4.5" and the housing 22 not be more than 7"×9" in area, and not more than 3" deep.

As shown in FIG. 2, the real time ammonia sensor 20 provides external connections 50 that facilitate the monitoring of ammonia levels within the poultry holding area 12a, as well communication with the house controller 30. In an exemplary aspect of the ammonia sensor 20 shown in FIG. 2, the bottom of the housing 22 provides five external connections 50, including two fluidic connections 52a, 52b, a communication connector 54, a power connector 56, and an auxiliary data port 58. In other aspects, the ammonia sensor 20 can include more or fewer external connections 50, as well as connections of different types.

The fluidic connections 52 include an intake port 52a ("IN") and an exhaust port 52b ("OUT"), which connect to the intake hose 16 and the exhaust hose 17, respectively. The intake port 52a and the exhaust port 52b connect the intake hose 16 and the exhaust hose 17 to components within the housing 22 of the ammonia sensor 20. Such components include, but are not limited to, a fluid circulation subsystem (FCS) 100 and a chemical sensor module (CSM) 200, both shown in FIGS. 3-7 and discussed in more detail below. These ports 52a, 52b may include nipples that connect to the respective intake hose 16 and exhaust hose 17. As discussed above, it is preferable that the nipples of the intake port 52a and the exhaust port 52b and intake hose 16 and exhaust hose 17 are of different sizes to preclude cross connection. Further, it is preferable that the intake hose 16 and all other parts exposed to air on the inlet side be made of materials that do not off-gas, and do not absorb ammonia or other gases. This material, as discussed above, can include, but is not limited to, polytetrafluoroethylene.

In an aspect, the communication connector 54 (CTRL) is configured to output real-time information to various components associated with the ammonia monitoring system 10. In an aspect, such real-time information can include, but is not limited to, $NH_3$ and humidity levels as well as temperature. In an aspect, the communication connector 54 can be configured to output the real-time information to the house controller 30. In an aspect, the house controller 30 is configured to control lighting, ventilation, heating, humidity, and other parameters in the poultry holding area 12a. In an exemplary aspect, the house controller 30 is configured to control the ventilation of the poultry house 12 based upon the notification from the ammonia monitoring system 10 that the concentration of ammonia in the poultry housing area 12b has reached a certain level or passed a given threshold. Specific format and content for the real time information transmitted by the communication connector 54 are discussed below. Various connectors can be used with the communication connector 54, dependent on the needs of the house controller 30 and various components. In some embodiments of the present invention, the various connectors may have a standard connector on the end that connects to communication connector 54 of the ammonia sensor 20, with the other end being defined by the type of house controller 30. The communication connector 54 could also be achieved wirelessly by adding an external wireless dongle at the communication connector 54, or by using an internal modem.

In an aspect, the power connector 56 is configured to accept a plug-in power cable. The power cable can be a standard 110 VAC, 3-prong cable approved for use in the United States. Other power cables may be utilized as well. In some embodiments of the present invention, the power cable is hardwired into the ammonia sensor 20, with an appropriate strain relief. Power can be provided through various means known in the art. In another aspect, the ammonia sensor 20 can include an internal power source, including, but not limited to, a battery, solar panel assembly, or the like. In such aspects, a power connector 56 may not be necessary.

In an aspect, the ammonia sensor 20 can include auxiliary data ports 58. In an aspect, the auxiliary data ports 58 can be configured to include a USB port. In such aspects, the USB port of the ammonia sensor 20 can be configured to be compatible with standard USB cables. In other aspects, the ammonia sensor 20 can have other auxiliary data port types 58 that are compatible with various other connectivity means known in the art. For example, some embodiments of the ammonia sensor 20 can include a dedicated memory stick configured to removably couple to the auxiliary data port 58. The memory stick may include pre-loaded software for installing a simple application on a user's computer. The memory stick can be configured to connect to the ammonia sensor 20 to download data, which can then be transferred to a user's own computer, where software will retrieve it for the user to store, display, and manipulate.

In an aspect, an auxiliary data port 58 can be configured to provide the interface for calibration and diagnostics, as well as the uploading of new software. In such aspects, the auxiliary data port 58 can be provided as a separate output from the communication connector 54 to allow a user to connect to the auxiliary data port 58 and download historical or real-time data without interrupting the output signal to the house controller 30. Preferably, the communication connector 54 should be of a different physical connection type from the auxiliary data port 58 to preclude cross-connection.

As discussed above, the ammonia sensor 20 includes hardware and software components. In an aspect, the hardware components of the ammonia sensor 20 include three interdependent subsystems organized by hardware function—not by physical location or implementation. In the aspect shown in FIG. 3, the subsystems include a fluid circulation subsystem (FCS) 100, a chemical sensor module (CSM) 200, and a monitor controller (MC) 300. The FCS 100, CSM 200, and the MC 300 work together to monitor the concentration of ammonia in the poultry holding area 12b, and alert the house controller 30 to ventilate the poultry holding area 12b upon reaching a certain threshold concentration.

In an aspect, the FCS 100 can include a pump 110 and valve 108 that interact with an ammonia filter 104, the junction box 14, and all external hoses (intake 16 and exhaust 17 and respective filters 18, 19) and internal hoses discussed in more detail below. Components of the FCS 100 can be connected to the CSM 200. In an aspect, the CSM 200 includes a laser 240, waveguide 230, camera 250, and mount (shown in FIGS. 5-6). In an aspect, the FCS 100 and CSM 200 are connected to the MC 300. In an aspect, the MC 300 is an embedded system or single board computer which controls the FCS 100, the CSM 200, image processing from the CSM 200, data processing from any additional sensors, the touchscreen display 40, user Interface connections, and power conditioning. In an aspect, the MC 300 provides power and commands to all electronic components of the FCS 100 and CSM 200, and receives data from the CSM 200. The MC 300 can also input and output data to the communication connector 54 and auxiliary data ports 58, including receiving commands. In the preferred embodiment, 110 VAC power enters through the power connector 56 and is converted to required levels by the internal electronics of the MC 300.

Figure 4:
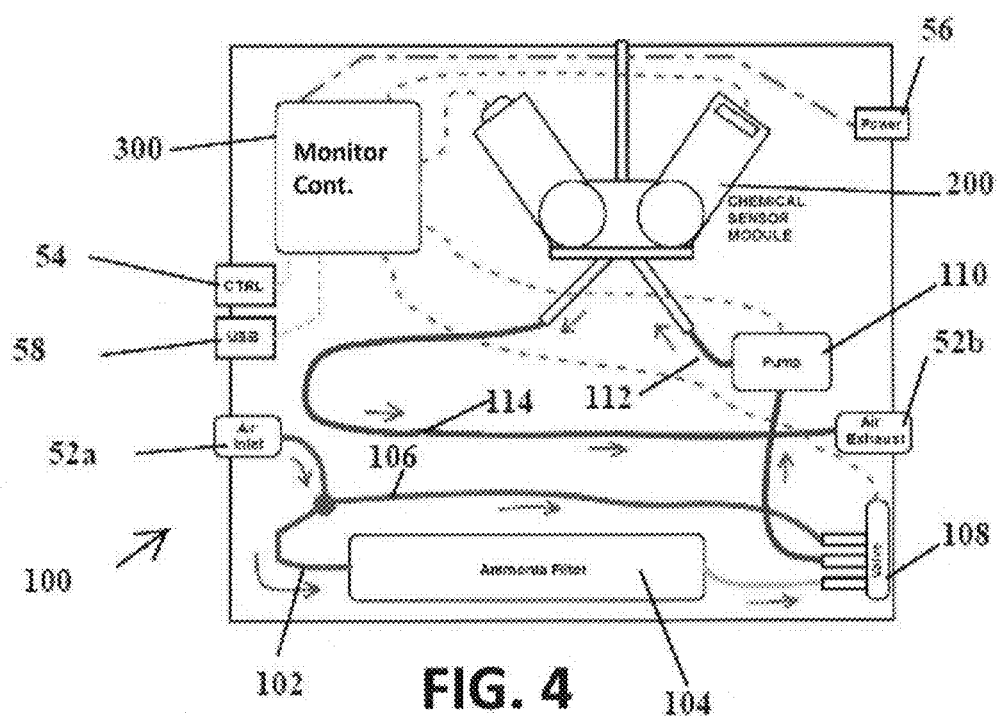
FIG. 4 is a schematic representation of the subsystems of FIG. 3.

FIG. 4 is a block diagram showing connections and flow in the FCS 100 to various components of the ammonia monitoring system 10. In one embodiment, fluid enters on the left through the intake port 52a (labeled air inlet in FIG. 4), and is immediately split into two paths: a filtered path 102 going through the ammonia filter 104, the unfiltered path 106 bypassing the ammonia filter 104. In an aspect, the ammonia filter 104 filters ammonia out of the fluid, but should not affect its humidity level, temperature, or other characteristics. The ammonia filter 104 can be made of a variety of filter material comprised of but not limited to, copper sulfate pentahydrate, copper bromide, and the like.

Both the filtered path 102 and the unfiltered path 106 terminate in inlets to a valve 108, which selects either the filtered fluid (i.e., from the filtered path 102 with the filter 104) or the unfiltered fluid (i.e., unfiltered path 106) to pass through via additional tubing 112 to a waveguide of the CSM 200. In an aspect, a pump 110 can control the flow of the fluid to CSM 200. By having a filtered path 102 and an unfiltered path 106, the ammonia sensor 20, and more specifically the CSM 200, can be configured to self-calibrate on a regular basis to reduce sensor drift and maintain accuracy. For each sense cycle, the filtered fluid is first measured to establish a zero-ammonia baseline, in order to cancel waveguide drift. The filtered path 102 and the unfiltered path 106 should be balanced in terms of the pressure drop through the path, the time travel for fluid through the path, and the relative humidity. In another aspect, to further ensure accurate measurement, the FCS 100 can utilize a temperature sensor and a temperature controlling mechanism (e.g., a fan or heating coil) to regulate temperatures of the fluids passing through the filtered path 102 and unfiltered path 106.

The pump 110, whose location in the stream can change (i.e., the pump 110 can be external to the ammonia sensor 20), either pushes or pulls fluid from the poultry holding area 12a through the ammonia sensor 20, including to the CSM 200, for ammonia level measurement. The fluid exits the CSM 200 via additional tubing 114 and passes through the exhaust port 52b, which passes the fluid to the exhaust hose 17. Table 1 below discloses parameters of the various components of the FCS 100 according to an aspect.

TABLE 1

Air Circulation Subsystem Parameters

| Parameter | Sym | Unit | Specification min | typ | max |
|---|---|---|---|---|---|
| Air Flow Through Sensor | | L/min | | 0.2 | |
| System Leak Rate | | mL/min | | | 5 |
| Leak Rate Through Valve | | % | | | 0.1 |
| Ammonia Filter Capacity | | days | | 75 | |

In an alternative aspect, the ammonia sensor 20 can contain two valves 108, and fluid is continually pumped through both the filtered path 102 and unfiltered path 106 so that there is no latency between the environmental characteristics of the fluid the filtered path 102 and unfiltered path 106. In such an aspect, fluid from the path not being pulled or pushed through the CSM 200 bypasses the CSM 200 and is coupled with fluid coming out of the CSM 200 to be exhausted through the exhaust port 52b.

Figure 16:
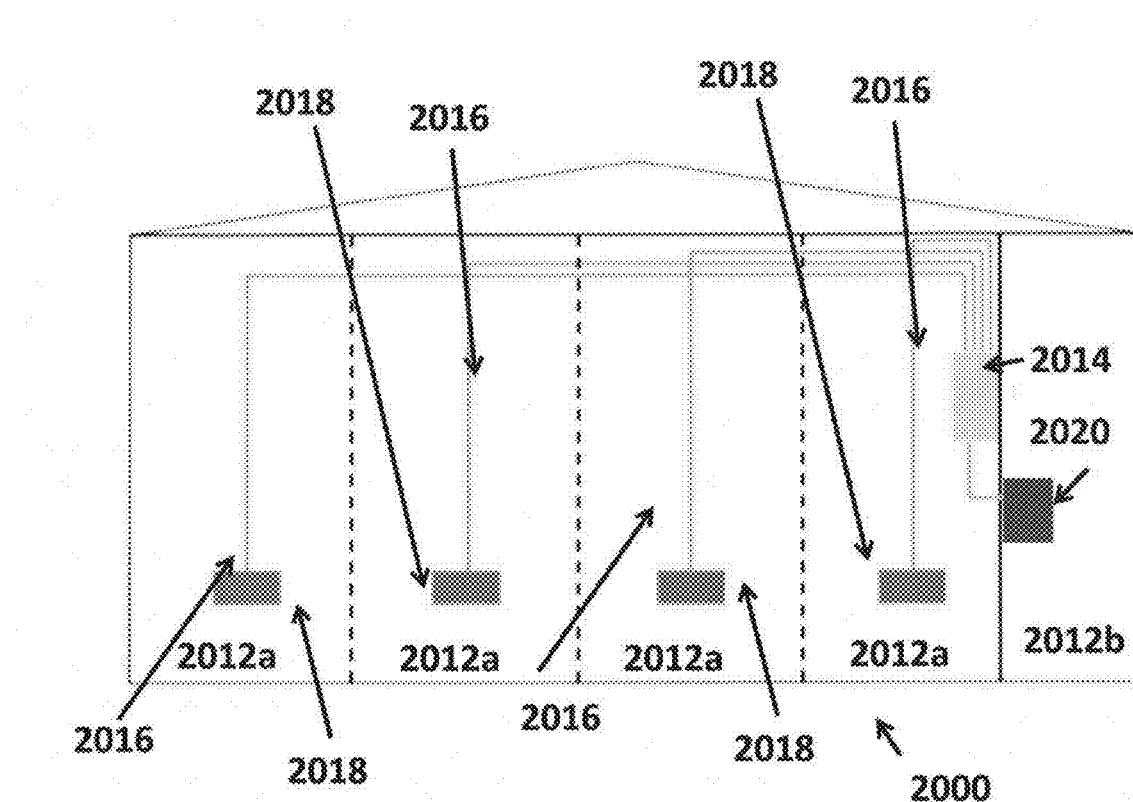
FIG. 16 is a schematic representation of an ammonia monitoring system monitoring several sections of a poultry house according to an aspect.

In another aspect, an ammonia monitoring system 2000 can be configured to provide a multi-valve switching mechanism for multi-point sampling in the poultry holding areas 2012a, particularly for the mega-coops, as illustrated in FIG. 16. As shown, multiple intake hoses 2016 and filters 2018 can be found in multiple poultry holding areas 2012a. The multiple intake hoses 2016 can be configured to fit a junction box 2014 with a multi-valve switching mechanism (not shown) that switches between multiple inlets. In such an aspect, the ammonia sensor 2020 (in control room 2012b) and the intake switching (within the junction box 2014) are synchronized by a controller in the ammonia sensor 2020. In an exemplary aspect, the switching mechanism can be modular so that additional intake lines 2016 can be added when needed. A significantly greater area can be covered with this method. However, since only one intake hose 2016 can be sampled at one time, the sampling rate per intake will be longer. The intakes 2016 not currently being sampled can be continuously purged by a pump in the junction box 2014; this will decrease the need to prime the lines when the ammonia sensor 2020 switches to a new intake 2016.

While it is important for the intake port 52a and exhaust port 52b to remain unblocked, the preferred embodiment of the ammonia monitoring system 10, and more specifically the FCS 100, is configured to operate without causing self-inflicted damage if either port becomes blocked for an indefinite period of time. Further, the ammonia filter 104 and/or neutral filter should be replaced as a part of normal maintenance at the end of each flock, nominally 8 weeks.

FIGS. 5-8 illustrate components of the chemical sensor module (CSM) 200. The CSM 200 can be configured to utilize optical interferometry to sense the amount of ammonia in the fluid. In an exemplary aspect, the CSM 200 contains a Mach-Zehnder interferometer. In other aspects, other optical interferometers, including, but not limited to, Michelson, Fabry-Perot, Twyman-Green, Sagnac, Rayleigh, and Jamin interferometers can be used. The interferometer includes a sense channel 234 coated with a polymer that selectively changes its index of refraction when exposed to ammonia, discussed in detail below.

Figure 5:
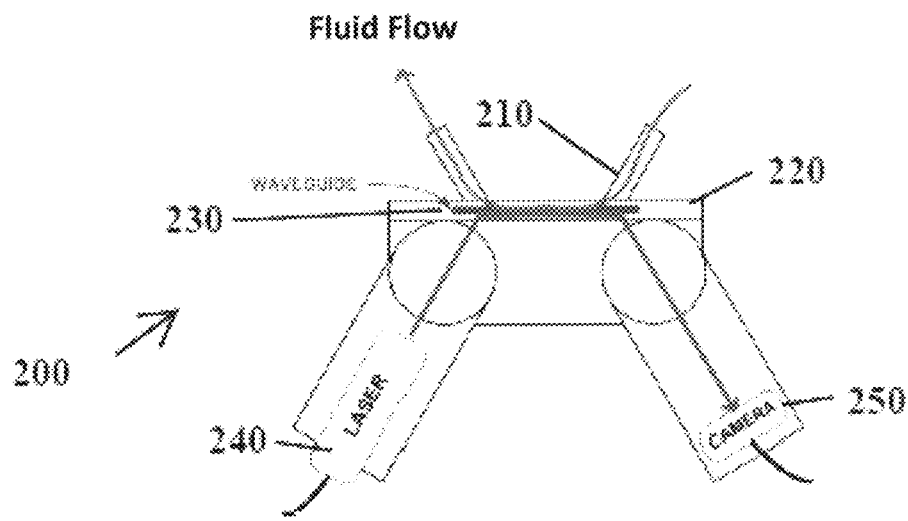
FIG. 5 is a cross-sectional side schematic view of the chemical sensor module of the ammonia monitoring system according to an aspect of the present invention.

Fluid, labeled as "fluid flow" at the top of FIG. 5, is pumped in from the right through an inlet tube 210, and passes through a sealed chamber 220 (i.e., flowcell) over a waveguide 230. At the same time, a low power laser 240 launches a beam of monochromatic light into the waveguide 230. Interference patterns are displayed on a camera 250 (e.g., a camera chip 250) or otherwise captured by another form of optical detector, at the output side of the CSM 200. In an aspect, the CSM 200 utilizes a UI-1542LE-M model camera 250 from IDS Imaging.

Figure 6:
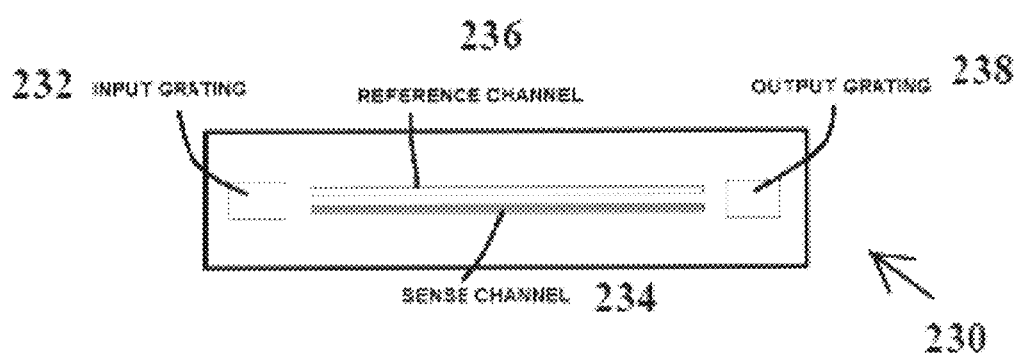
FIG. 6 is a schematic top view of a waveguide of a chemical sensor module according to an aspect of the present invention.
Figure 7:
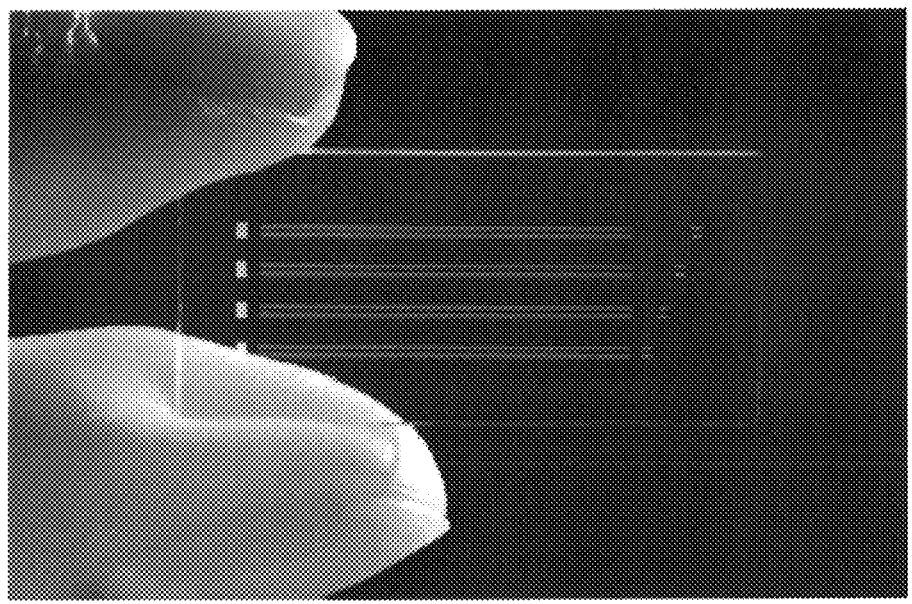
FIG. 7 is a top view of a waveguide with four separate channel pairs according to an aspect of the present invention.
Figure 8:
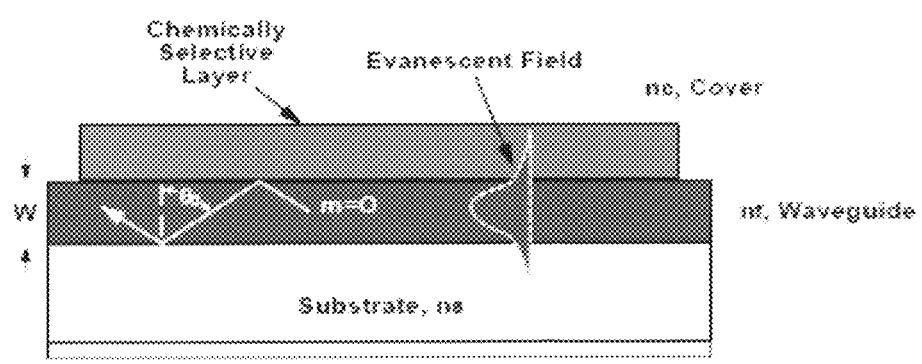
FIG. 8 is a cross-sectional view of a waveguide according to an aspect of the present invention.

In an aspect, as illustrated in FIGS. 6-8, the waveguide 230 is a stacked thin film structure with a base of optical glass, a thin core layer of a higher-index material, and an upper cladding layer into which are etched the long, narrow channels 234, 236. In an aspect, the waveguide 230 consists of an input grating 232, one or more pairs of parallel channels—e.g., a sense channel 234 and a reference channel 236—and one or more output gratings 238. For example, in the exemplary aspect illustrated in FIG. 7, the waveguide 230 can be configured to have four pairs of sense channels 234 and reference channels 236, as well as four input gratings 232 and output gratings 238. The CSM 200 can be configured for the laser 240 to be oriented under the waveguide 230 so that the light of the laser 240 enters the input grating 232 from the bottom of the waveguide 230, and is refracted to travel down the length of the sense channel 234 and reference channel 236 (left to right in FIGS. 5-7).

In an aspect, the sense channel(s) 234 is filled with a chemically sensitive polymer whose index of refraction changes in proportion to adsorption of the corresponding chemical, causing the speed of light in that polymer to change correspondingly. Further, the chemically-sensitive polymer that is utilized is configured to adsorb the chemical as the polymer is exposed to the chemical, and desorbs as the polymer is exposed to a fluid without the chemical. In an exemplary aspect, the chemically-sensitive polymer is an ammonia adsorptive polymer, whose index of refraction changes in proportion to ammonia adsorption. The polymer used to coat the sense channel(s) 234 in the preferred embodiment of the present invention is a polyvinylphenol (PVP) titrated to a pH of 7 with potassium hydroxide covered with a top coat of ethyl cellulose. The reference channel 236 is covered so as to not be affected by the polymer coating (i.e., it is not adsorptive of ammonia).

In an exemplary aspect, the sense channel(s) is coated with PVP at a thickness of the PVP is 1600 Angstroms, while the thickness of the ethyl cellulose is 5000 Angstroms. In other embodiments of the invention, other coatings and thicknesses can be used. The speed of light in the sense channel 234 and the reference channel 236 will be different to a degree proportional to the amount of ammonia in the fluid sample. In an aspect, both the sense channel 234 and the reference channel 236 are either equally adsorptive to water vapor, or the CSM 200 is calibrated and inclusive of a humidity sensor, or the ammonia monitoring system 10 contains filters which dampen humidity transients in the fluid coming into the CSM 200, so that the overall effect of humidity on system performance is immaterial. In an exemplary aspect, both the sense channel 234 and the reference channel 236 are also covered with a protective coating, permeable to ammonia, to reduce fouling.

In an aspect, as the sense channel 234 and reference channel 236 are exposed to the ammonia-containing fluid (i.e., the fluid that has gone through the unfiltered path 106, such path potentially containing a "neutral" filter which does not affect the chemical composition of the fluid but does balance pressure and flow through the unfiltered path with that of the filtered path 102), ammonia adsorbs to the sense channel 234 in proportion to the amount of the exposure (i.e., the more time exposed to ammonia, the more ammonia is adsorbed). Once the waveguide 230 has been exposed for the desired time, the waveguide 230 can then be exposed to the filtered fluid (i.e., the fluid that has gone through the filtered path 102 and filter 104). Light from the laser 240 is coupled into the waveguide 230 and a portion of this coupled light (its evanescent field, as shown in FIG. 8) travels through the polymer coating that has been applied to the surface of the sense channel 234. Laser light also travels down the adjacent reference channel 236. The interference pattern generated by the optical interaction of light from the sense channel 234 and the reference channel 236 is imaged on the camera 250. The sense channel 234, and more specifically the ammonia sensitive polymer, will capture or release ammonia molecules in proportion to the concentration of ammonia in the fluid, changing the index of refraction of the ammonia sensitive polymer on the sense channel 234, which therefore alters, in a quantifiable way, the interference pattern created by the recombination of the light passing through the sense channel 234 and the reference channel 236. The phase shift of the interference pattern, which, in an exemplary aspect, is proportional to the concentration of the ammonia, is determined using a processor running image processing algorithms, discussed in more detail below.

After exiting the right-hand side of the sense channel 234 and the reference channel 236, both light beams are again refracted and combined by the output grating 238, creating, as mentioned above, an interference pattern on the surface of the two-dimensional camera 250 or other form of optical detector. If ammonia is present, the light waves in the sense channel 234 and the reference channel 236 will travel at different speeds, and one will arrive at the output grating 238 before the other, causing a phase shift in the interference pattern on the camera chip 250 that is proportional to ammonia concentration. The MC 300 analyzes the image from the camera chip 250 and measures the phase shift (the movement in the interference pattern over time as the ammonia concentration changes) to determine the ammonia concentration using calibration coefficients associated with the ammonia sensor 20 already accessible (e.g., stored within the MC 300). These coefficients may be updated through various means as well.

While FIG. 6 depicts a single pair of channels 234, 236 on the waveguide 230, waveguides 230 may also contain multiple channel pairs (e.g., see FIG. 7), each with the same or different polymer pairs, to sense multiple analytes in the air sample, or to increase reliability. Table 2 below provides the characteristics for the CSM 200 according to one exemplary aspect.

TABLE 2

Chemical Sensor Module Characteristics

| | | | Specification | | |
| --- | --- | --- | --- | --- | --- |
| Parameter | Sym | Unit | min | typ | max |
| Laser Wavelength | λ | nm | 665 | 670 | 675 |
| Polymer Composition | | | | | |
| System Sensitivity | S | ppm | 5 | | |
| Full Scale Range | FSR | ppm | 1 | | 100 |
| Accuracy, after calibration and signal conditioning by Monitor Controller | | ppm | −3 | | 3 |
| Damage Threshold | | ppm | 500 | | |
| Sense Time | $t_{sns}$ | sec | | | |

In an aspect, the MC 300 is resident in the ammonia sensor 20 and is not accessible to the user except functionally via the user interface 40 or external connectors 50. In an aspect, the MC 300 includes the power control system of the ammonia sensor 20. In an aspect, the power control system of the MC 300 includes a current monitor to detect off-nominal conditions, discussed in more detail below. In an aspect, the MC 300 includes on-board memory. In an exemplary aspect, the memory of the MC 300 is configured to be of a nonvolatile type and provides enough on-board memory to store three days' worth of readings at the shortest reading interval, which can be set by the user. In such aspects, the memory of the MC 300 is erased on a first-in, first-out basis when the memory becomes full. In an aspect, the memory of the MC 300 is configured to maintain a system log file and user-defined identification data. In an exemplary aspect, the memory of the MC 300 is configured to have 1 16 k of user-defined identification data and at least 512 k to maintain a system log file. In an aspect, the MC 300 is configured to include a real time clock (RTC) which continues to track time even when the system 10, or more specifically the ammonia sensor 20, is powered down. It is preferred that the RTC shall maintain an accuracy of better than ±6 hours per year for up to three years.

In other embodiments, the location and association of the components of the ammonia monitoring system 10 may vary from what is described above. For example, the junction box 14 may house various components, including, but not limited to, the pump 110, valve 108, and ammonia filter 104. In other embodiments, the junction box 14 may also include the CSM 200 and the FCS 100, with the MC 300 being housed separately in the housing 22 of the ammonia sensor 20. In addition, some elements as discussed above may not be utilized in other embodiments. For example, in an aspect, the ammonia monitoring system 10 can be configured not to include a junction box 14: the various pumps 110, valves 108, the filter 104, and hoses that form the filtered path 102 and unfiltered path 106 can be exposed, or be contained within the housing of the ammonia sensor 20.

In an aspect, the MC 300 is configured to control overall operations of the ammonia sensor 20. In an aspect, the MC 300 is configured to: control a user interface 40, which can comprise a touchscreen display; interface with the communication connector 54 and auxiliary data ports 58; interface with the user via the user interface 40 to set options and conduct maintenance; manage power input to the ammonia monitoring system 10; detect system faults and respond to them; save ammonia concentration data to a time-stamped data file; save significant events to a System Log; and detect and react to exceptions and errors. These functions can be implemented and run through various applications, including, but not limited to, Labview software from National Instruments.

Figure 9:
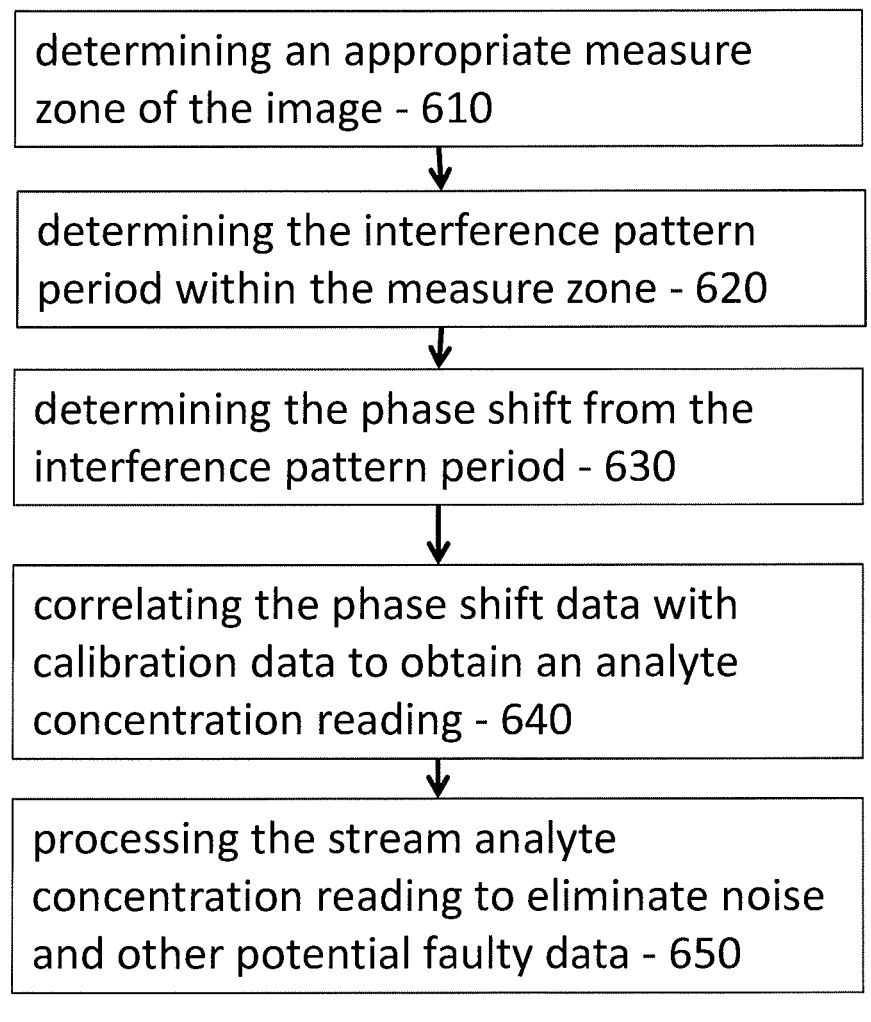
FIG. 9 is a flow chart of a method performed by components of an ammonia monitoring system according to an aspect.

In an aspect, the MC 300 is further configured to control the operation of the FCS 100 and the CSM 200. In an aspect, the MC 300 is configured to control various functions of the CSM 200. In an aspect, the MC 300 can be configured to determine the ammonia concentration as well. The MC 300 is configured to use applications, including an ammonia detection application discussed in detail below, to determine the ammonia concentration. In addition, the MC 300 can be configured to process the images from the CSM 200, including image cropping, to determine the ammonia concentration. In an aspect, the MC 300 can determine the ammonia concentration through a method 600 as illustrated in FIG. 9. In an aspect, the ammonia concentration is done by determining an appropriate measurement zone of the image (step 610), determining the interference pattern period within the measurement zone (step 620), determining the phase shift that has occurred from the interference pattern period (step 630), correlating the phase shift data with calibration data to obtain an analyte concentration reading (step 640), and processing the stream analyte concentration reading to eliminate noise and other potential faulty data (step 650). In an exemplary aspect, the ammonia detection application can perform the method 600.

The MC 300 can determine the appropriate measurement zone for the images collected by the camera 250 in various ways (step 610). In an aspect, the MC 300 can determine the appropriate measurement zone by evaluating the relative high and low intensities of the images captured by the camera 250. Other known methods can be used to determine the appropriate measure zone.

Once the measurement zone has been determined, the MC 300 can determine the interference pattern period within the measurement zone (step 620). In an aspect, the MC 300 can utilize image processing algorithms to determine the interference pattern period. In an exemplary aspect, the MC 300 can utilize a spatial Fourier transform algorithm. In such an aspect, the spatial Fourier transform algorithm is used to get the spatial frequency components of the interference pattern, and more specifically to find the dominant spatial frequency component. In other aspects, other algorithms or methods can be used to determine the interference pattern frequency and components other than the dominant frequency component of the interference pattern can be used to determine concentration.

Once the interference pattern's dominant spatial frequency has been determined (step 620), the MC 300 can find the phase shift that has occurred from the interference pattern period (step 630). In an exemplary aspect, the MC 300 can use the dominant spatial frequency component that was determined by the Fourier transform algorithm. In such an aspect, a phase demodulation can use the dominant frequency component to measure the phase shift. In other aspects, other processes can be used to determine the phase shift measurement.

Upon determining the phase shift measurement data, the MC 300 can then correlate the phase shift data with calibration data to obtain an analyte concentration reading (step 640). In an exemplary aspect, the phase shift data can be multiplied by a calibration coefficient to determine the ammonia concentration reading.

Once the analyte concentration reading is determined, the MC 300 can process the concentration reading to eliminate noise and other potential faulty data (step 650). This can be done by using weighted averaging algorithms or other signal processing techniques. In addition, other environmental conditions can be considered as well to eliminate faulty data. For example, the analyte concentration reading can be adjusted according to the current humidity level. Such information can be obtained through humidity sensors. The analyte concentration reading can then be displayed by the user interface 40, and can be utilized to determine when the ammonia level in the poultry holding area 12a has reached a level that necessitates the activation of the house controller 30 to ventilate the holding area 12a.

As discussed above, the MC 300 is configured to control the operation of the ammonia monitoring system 10. In an aspect, the MC 300 is configured to provide simple operations for a user. As such, in exemplary aspects of the system 10, the ammonia sensor 20 has a limited number of modes: a measurement mode, a standby mode, a system error mode, a maintenance mode, and a calibration and diagnostic Mode. While it is preferred that the ammonia sensor 20 be limited to these five modes, other embodiments may include more optional modes, different modes, or fewer modes.

Figure 10:
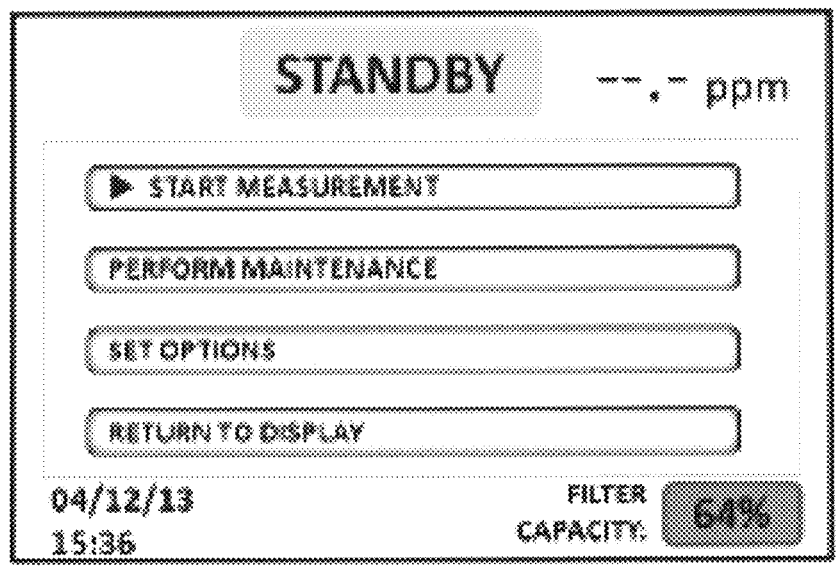
FIGS. 10-12 are representations of a user interface display of a real time ammonia sensor according to an aspect.
Figure 11:
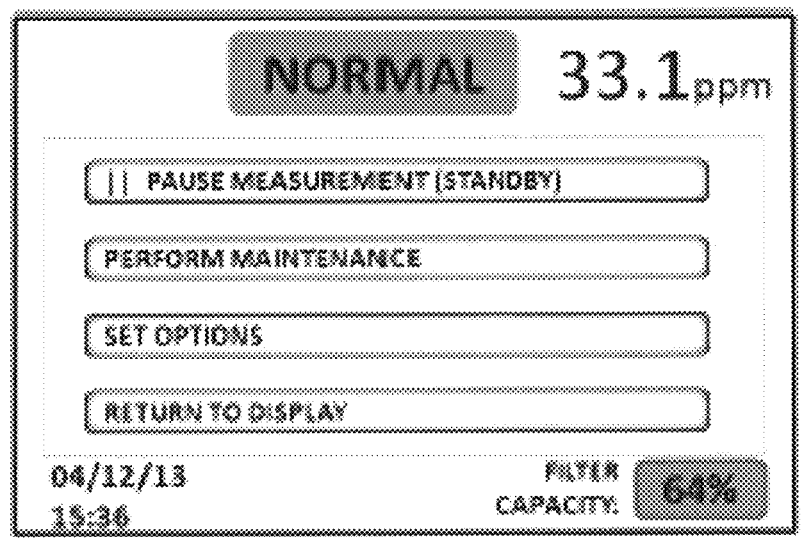
Figure 12:
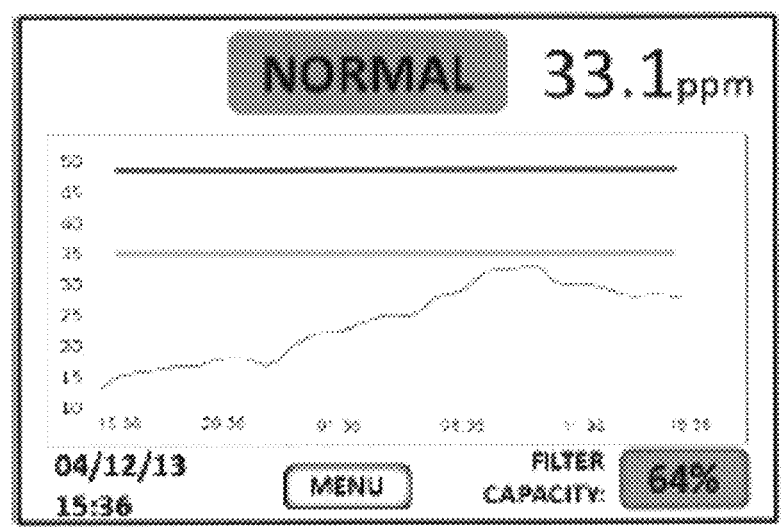

FIGS. 10-12 depict screen illustrations of the modes discussed above as displayed to a user according to an aspect and are not meant to suggest specific layout or artwork for the screen. The screens shown are meant to correspond to the display/user interface 40 of FIG. 2. As shown in FIGS. 10-12, the display 40 includes certain information provided to the user, including the status of which mode the ammonia sensor 20 is presently operating, and any corresponding readings. For example, the display 40 can include a measurement status indicator. As shown in FIG. 8, the measurement status indicator shows that the system is in standby mode. In standby mode, the ammonia sensor 20 is not operational, and displays "STANDBY" on its screen. This mode is generally used during times when no animals are present in the poultry holding area 12a.

When in the measurement mode, the ammonia sensor 20 can be configured to continuously measure, display, and record ammonia levels according to system presets, which can be adjusted by the user. In an additional aspect, when in measurement mode, the ammonia sensor 20 can be configured to notify the house controller 30 with the ammonia level reaches a certain level or threshold. In an aspect, the ammonia sensor 20 can continuously pass along information related to the ammonia levels to the house controller 30, and the house controller 30 can be configured to determine with the supplied ammonia levels surpass safe ammonia levels that necessitate ventilating the poultry holding area 12a.

As shown in FIG. 11, the measurement status indicator shows that the system is in the MEASUREMENT mode, displaying a "NORMAL" to indicate the system is presently taking measurements, and the last measurement was within the Normal threshold set by the user. In an aspect, when the ammonia sensor 20 finds that a last measurement of ammonia is above a caution threshold set by the user, a "CAUTION" measurement status indicator can be displayed. Likewise, when the ammonia sensor 20 finds that a last measurement of ammonia is above a user-set Warning threshold, a "WARNING" status indicator can be displayed. Other embodiments may use descriptive words other than "Normal," "Caution," or "Warning." In other aspects, colors (e.g, green, yellow, and red) can be associated and displayed to indicate the status of the ammonia levels measured.

In addition to the measurement status indicator, the display 40 can include other information. Such information can include a last measurement numerical indicator, a data/time display, and the filter capacity display. The numerical indicator indicates the last ammonia level reading taken. In standby mode, this indicator reads "--.-", as shown in FIG. 10. Further, it is preferable that the numerical indicator display the amount with 0.1 ppm precision. The data/time display shows the present date and time, with minute precision, and is user adjustable in the preferred embodiment. Also in the preferred embodiment, the date/time display adjusts for daylight savings time (US and Europe) and leap years. Lastly, the filter capacity display indicates the status, present capacity, or remaining life of the ammonia filter. In an exemplary aspect, the MC 300, through various means discussed below, keeps track of the total amount of ammonia to which the ammonia filter 104 has been exposed, as well as the time of exposure, and calculates remaining filter life. In an aspect, the numerical indicator can have colors associated with the remaining capacity of the filter 104: green for high capacity, yellow at a lower value, and red at a still lower value. In an aspect, when the $NH_3$ filter capacity is at zero, the ammonia sensor will no longer take readings, and displays a "change filter" message. The default threshold values for the color changes can be changed based upon the user's preference. In an exemplary aspect, the number is automatically reset to its maximum each time the user goes through maintenance mode. In some embodiments of the present invention, the filter capacity display will notify the user when a new filter has been installed improperly.

Referring to FIGS. 10-11, the display 40 can be configured to include Main Menu Controls. In an exemplary aspect, the Main Menu Controls displayed can include a Start/Pause Measurement button, a Performance Maintenance button, a Set Options button, and a Return to Display button.

In an aspect, the Start/Pause Measurement button toggles between 'Start' and 'Pause' measurement. When pushed from Standby mode, it places the system in Measurement mode. When pushed from Measurement mode, it places the system in Standby mode. The Perform Maintenance button launches Maintenance mode, described in more detail below. The Set Options button opens a lower level of menus and keypad displays that allow the user to change system options. The Return to Display button returns to the graphical display of historical measured $NH_3$ levels, as shown in FIG. 12. When in Standby Mode, the display is static and shows the most recent readings. When in Measurement Mode, the display is dynamic and continues to update. The Measurement Status Indicator, Last Measurement Numerical Indicator, Filter Capacity Indicator, and Date/Time Display continue to be displayed, independent of whether the graphical display or the menu is included in the embodiment.

As discussed above, the Graphical Display is initiated from the "Return to Display" button on the Main Menu. FIG. 12 illustrates the Graphical Display in Measurement Mode. As shown, the only control on the Graphical Display screen is the "Menu" button, which returns to the Main Menu (while remaining in either Standby or Measurement Mode). In other embodiments of the present invention, other buttons may be included on the Graphical Display.

The Graphical Display shows historical ammonia level readings. In Measurement Mode, it updates in real time. In Standby Mode, it shows the most recent readings. The 'x' axis is time; 'y' axis is ammonia level in ppm. Both axes are user-adjustable and can autoscale, as necessary and as desired, to accommodate the data. In an aspect, the lines can be displayed in a certain color for certain threshold levels of ammonia (e.g., yellow and red lines indicate the user-adjusted "Caution" and "Warning" thresholds, respectively). Date range limits on the display can be set by the user.

In an aspect, the parameters are displayed as a series of points connected by straight lines, during periods where the ammonia sensor 20 was in Measurement Mode. If the ammonia sensor 20 was placed in Standby Mode at any point during the time interval displayed, values during those durations are not displayed on the display, appearing as gaps in the line. While FIG. 12 shows the display illustrating the numbers using a traditional x and y axis that correspond to time and ammonia levels, other types of graphical representations may be used in other embodiments, including, but not limited, bar charts with min, max, and current levels.

In an aspect, the ammonia sensor 20 and the overall ammonia monitoring system 10 enters Measurement mode: (a) when "Start Measurement" is selected from the Main Menu; or (b) when the system returns from System Error Mode, if Measurement Mode was the last known mode (note: on return from a power dropout, the system starts in Standby Mode).

In Measurement Mode, the display 40 illustrates the Graphical Display as in FIG. 12. The user may toggle between the Graphical Display and the Main Menu without leaving Measurement Mode. The ammonia sensor 20 continuously takes ammonia level readings at the time interval specified by the Measurement Interval parameter, according to the behavioral flow shown in FIG. 13.

When the Measurement Mode is started (1000), the graphical display is changed (1001) to show something similar to that presented in FIG. 12. The pump 110, laser 240, and camera 250 are turned on and initialized as appropriate (1002). Using image processing algorithms, which in one embodiment includes the use of Fourier transforms, the system 10 begins tracking both the phase shift that occurs in the interference pattern detected by the camera (1003) In an aspect, the system 10 can also track the relative humidity (1004). Using a real-time clock, a counter is set (1005) for a duration. In an exemplary aspect, the counter is set for 20 seconds. In other aspects, the duration can vary depending on the environment in which the ammonia monitoring system 10 is utilized. Once the counter is set, the valve 108 can be switched (1006) so that fluid filtered by the ammonia filter 104 (filtered path 102) travels through the flow cell 220 and over the waveguide 230 (i.e., unfiltered fluid from the unfiltered path 106, containing, in an exemplary aspect, the neutral filter, has already been exposed to the waveguide 230 and the sense channel 234, with ammonia being adsorbed).

Once filtered fluid is flowing, the MC 300 can then acquire phase shift data through images of the interference pattern from the waveguide 230 captured by the camera 250 and utilizing image processing algorithms (steps 1007 and 1008). In an aspect, the ammonia monitoring system 10 first takes the derivative (or slope) of the phase data, and then filters the derivative phase shift data to remove high frequency noise components (step 1007). The maximum negative value of this processed data is then found (1008). Since the speed of the chemical adsorption and desorption of the ammonia responsive polymer coating of the sense channel 234 is proportional to the concentration of ammonia in the sample, the derivative approach can be used, preserving filter capacity. The value found in (1008) is then multiplied by a calibration coefficient, which can be adjusted according to the current humidity level (i.e., performed at step 1005) (1009).

If the value obtained is within a reasonable range and not dramatically different from the last measurement (1010), and if no other errors or failures are detected in the sensor, the value is then logged and passed along for graphical display as well as for communication to the Controller (1012). Errors would cause the sensor to enter System Error Mode (1011). If no errors are found, the system 10 waits until the countdown has reached zero (1013) and, when this has occurred, the valve 108 is switched so that the poultry house fluid is passed unfiltered through the flow cell 220 to the waveguide 230 (1014). The countdown clock is then reset (1015), allowing the waveguide 230, and more specifically the polymer of the sense channel 234 to adsorb ammonia from the poultry house. In an exemplary aspect, the clock is reset can be set to 100 seconds. In other embodiments, other time periods can be utilized. When the countdown again reaches zero (1016) and the ammonia sensor 20 has not been asked to pause or standby (1017), the ammonia sensor 20 then resets the countdown and switches back to the filtered state (1005 and 1006). Otherwise, the system 10 enters standby mode (1018).

In an aspect, the ammonia sensor 20 exits measurement mode when: (a) the user selects "Pause Measurement Mode" from the Main menu; (b) a System Error occurs, or (c) the system is powered down. The ammonia sensor 20 enters Standby Mode when: (a) the system is powered up; (b) the user selects "Pause Measurement" from the Main Menu, or; (c) the system recovers from a System Error and the last state before the error was Standby Mode. When the Graphical Display is shown on the user interface 40 during Standby mode, only historical data is presented, with the time intervals during which the system is in standby having no data appearing as gaps in the curve. In one embodiment of the present invention, if the user invokes Standby mode while the ammonia sensor 20 is taking a measurement, the ammonia sensor 20 interrupts the measurement, and then enters Standby Mode.

In Standby mode, the various components of the ammonia monitoring system 10 can be put into the following status: the valve 108 can be set to "Sense" (unfiltered) input, to minimize flow through the ammonia filter 104, the pump 110 can be turned off, and the CSM 200, including the laser 240 and camera 250, can be turned off as well. Further, the communication connector 54 can hold a 'no data' reading.

In an aspect, the ammonia sensor 20 enters SYSTEM ERROR mode when it encounters certain error conditions. In some embodiments of the present invention, the System Error Mode is identical to Standby Mode, except that it is initiated by certain System Errors that require measurements to stop in order to prevent possible damage to the ammonia sensor or the reporting of 'junk' data. In System Error Mode, the Status Indicator shown on the user interface 40 can read "SYSTEM ERROR". In an aspect, when the error condition is corrected, the ammonia sensor 20 can exit System Error Mode and return to the last saved mode, either automatically or by user action. The System Log can record time & date for entry into, and exit from, System Error mode.

Maintenance mode places the ammonia monitoring system 10 in a safe state and guides the user through maintenance actions to be performed at the end of each flock cycle. Maintenance on the ammonia monitoring system 10 is intended to be carried out at the end of each flock cycle, but can be performed any time the user desires. The ammonia monitoring system 10 may incorporate a maintenance countdown, which alerts the user to when the system needs regularly scheduled maintenance. In addition to keeping a 'maintenance countdown', the ammonia monitoring system may keep a separate 'Replacement Countdown', and shall alert the user via a Touchscreen text message when a replacement ammonia sensor is due.

Figure 14:
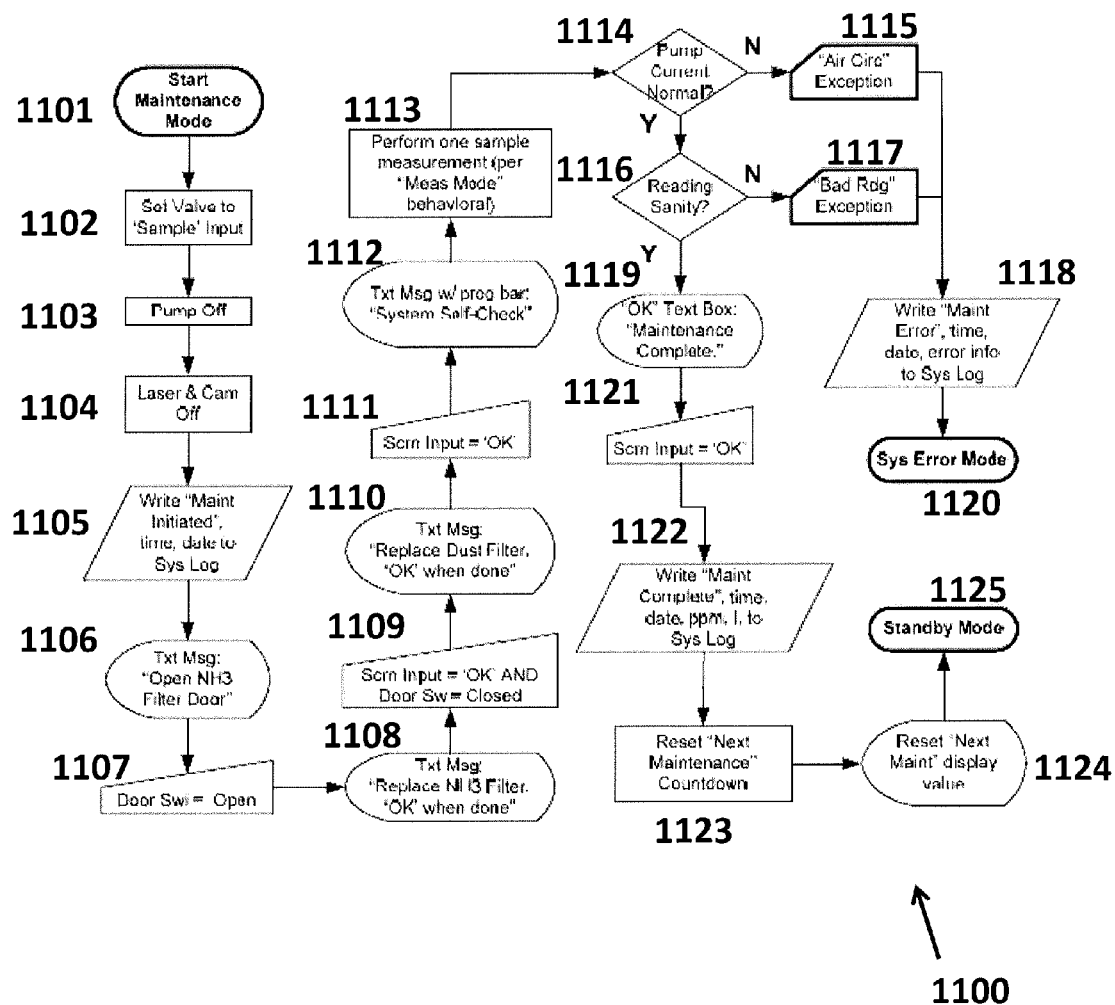
FIG. 14 is a flow diagram of a method performed by the ammonia monitoring system of FIG. 1.

FIG. 14 illustrates an exemplary aspect of system behavior in Maintenance Mode (method 1100). The User enters Maintenance mode by selecting "Perform Maintenance" from the main menu. The ammonia sensor configures the system as if in Standby Mode. A series of Text Messages on the Touchscreen guides the user through the maintenance steps, and the ammonia sensor performs several self-tests to ensure maintenance was carried out properly. The screen messages may include graphics that illustrate the task to be performed. In an aspect, the System Log records the start and end time/date of each maintenance.

As shown in FIG. 14, the maintenance mode is started by selecting the maintenance mode (step 1101). When started, the system 10, through the MC 300, sets the valve 108 to sample input (open to unfiltered path 106) (step 1102), turns the pump 110 off (step 1103), and turns the laser 240 and camera off (step 1104). In addition, the MC 300 can call upon the system log to record the initiation of the maintenance (step 1105). The ammonia sensor 20, via the user interface 40, can then prompt the user to open the filter door (step 1106). The MC 300 can then wait to receive confirmation that the filter door has been open, via a switch or some other means of sensing the door is open (step 1107). Upon receiving the notice of the door being opened, the MC 300 can then prompt the user to replace the ammonia filter 104, and potentially the neutral filter as well, on the user interface 40 (step 1108). In addition, the MC 300 can prompt the user to confirm, via the user interface (e.g., select OK tab) when done.

Upon receiving confirmation of the replacement (e.g., selection of the OK and closing of the door) (step 1109), the MC 300 can prompt the user to change the dust and feather filter 18 and exhaust filter 19 of the intake hose 16 and exhaust hose 17 (step 1110). In an aspect, the MC 300 can prompt the user to confirm the change by providing notification (e.g., OK tab). In other aspects, sensors employed at these filters 18, 19 can be utilized, reporting back to the MC 300. Once the cleaning has been confirmed (step 1111), the MC 300 can notify the user via the interface 40 that a system self check will be performed (step 1112). The MC 300 can then perform a self check by using a sample measurement for each measurement mode (step 1113). Once completed, the MC 300 can call upon the pump to see if the current is normal (step 1114). If the reading is not normal, a fluid circulation exception is generated (step 1115), and a maintenance error, along with the time, data, and error info is recorded to the system log (step 1118). If the pump circulation is normal, then the MC 300 checks to see if the reading is physically possible, perhaps by comparing it to recent readings (e.g., checking the sanity as shown in FIG. 14) (step 1116). If the reading is not, a bad reading exception is generated (step 1117), and the maintenance error is recorded as well (step 1118). If the reading is acceptable, the MC 300 notifies the user, stating that maintenance is complete, and provides a means of confirmation to the user (e.g., the OK tab) (step 1119). If the circulation or reading is not acceptable, the ammonia monitoring system 10 enters into system error mode (step 1120). Upon receiving the input of OK from the user (step 1121), the MC 300 will write that the maintenance has been completed in the system log, along with the time and date (step 1122). In an aspect, the concentration of ammonia will also be recorded as well. The MC 300 can then reset the next maintenance countdown (step 1123), including resetting the Next Maintenance display value (step 1124), and enter into standby mode (step 1125).

In an aspect, the ammonia monitoring system 10 can also have a calibration and diagnostic mode. The Calibration and Diagnostic mode facilitates calibrating the unit and performing certain diagnostics. In an aspect, the user can initiate the Calibration and Diagnostic mode by connecting a computer to an auxiliary data port 58 and running a calibration & diagnostic application from a computer. The application calibrates the chemical sensor by exposing the ammonia sensor to a test fixture containing known levels of ammonia mixed with air, as verified by a reliable, high-precision reference sensor. The calibration & diagnostic application may be configured to guide the operator through the calibration steps, and generate appropriate calibration coefficients, based on formulas and/or lookup tables. In an aspect, the calibration coefficients are stored locally on the ammonia sensor. In other aspects, the coefficients can also be stored in a global database.

The calibration & diagnostic application will also load identifying data into the local memory of the ammonia sensor 20 (discussed below), as well as the global database. Identifying data includes device hardware revision, firmware revision, serial number, date of manufacture, CSM 200 and waveguide 230 identifiers, with space reserved for user-defined data. Other identifying data may be included as well.

In an aspect, the calibration & diagnostic application can also have the ability to retrieve, store, and display real-time diagnostic data from the ammonia sensor 20, to assist in troubleshooting and understanding behavior of the ammonia monitoring system 10. Parameters may include, but are not limited to, pump current draw, total current draw, CSM current draw, CRC scan results, measurement history, system log, raw image data, and manual control of various subsystems.

In an aspect, a user can set options of the ammonia monitoring system 10, and the ammonia sensor 20. In an aspect, the user can set the options by selecting "Set Options" from the Main Menu to open a new menu with a number of options available to the user. These are specified in Table 3 below. The 'min' and 'max' refer to the highest and lowest levels of various components (e.g., ammonia coefficient, filter capacity, time, etc.) the user is allowed to select. In an aspect, the system 10 can be configured to have at least 5 ppm between "Caution" min and max, to prevent the user from setting thresholds that transition the system directly from "Normal" to "Warning", with no "Caution" zone in between. While Table 3 shows number of options available to the user in the preferred embodiment of this invention, other embodiments may vary in the number and variability of the options.

TABLE 3

User Options

| Option | Unit | min | max | Default |
|---|---|---|---|---|
| "Caution" Threshold (yellow) | ppm | 15 | W-5 | 35 |
| "Warning" Threshold (red) | ppm | Cmax + 5 | 100 | 50 |
| Set Clock | — | — | — | US EST |
| Measurement Interval | min | 2 | 720 | 2 |
| System Information | — | — | — | — |
| View System Log | — | — | — | — |
| Filter Capacity "Green" | % | | | 25 |
| Filter Capacity "Yellow" | % | | | 10 |
| Filter Capacity "Red" | % | | | 5 |
| Filter Capacity Shutoff | % | | 5 | <5 |

As discussed above, the ammonia monitoring system 10 may be configured to communicate data from the ammonia sensor 20 to other devices. In an aspect, the ammonia sensor 20 can be configured to automatically transfer such information to a device through the auxiliary data port 58. In an aspect, a program may guide the user through the process. To download data from the ammonia sensor 20, the user can connect a device, including, but not limited to, a memory stick, to the auxiliary data port 58 and wait for a "data download complete" message on the user interface 40 before removing the device. Connection and data download can take place in any ammonia sensor mode, without interrupting the ammonia sensor measurements or other functions.

In an exemplary aspect, the device (e.g., a memory stick configured for connection with another computer or a computer itself) can include the program guide and be further configured to provide an interface to prompt the user to utilize the acquired data. For example, a simple interface will allow the user to: view date ranges available for download; select a date range and download the data as a comma separated text file, for import to a program such as Microsoft Excel or other spreadsheet applications; display the data graphically for a selected date range; and/or download a copy of the System Log as a text file. In an aspect, the device can be configured to communicate over a network, including, but not limited to, the internet. In such an aspect, the device, with user's permission, can connect to a designated website and check for available firmware upgrades. If one is available, the device can download the information for later uploading to the ammonia sensor 20. If the ammonia sensor 20 is in measurement mode, the device can call upon the ammonia sensor to complete the present measurement and place the system 10 in Standby mode during upgrade, then automatically return the system to Measurement mode.

As discussed above, the MC 300 of the ammonia sensor 20 can maintain a system log for historical and diagnostic purposes according to an aspect. In such aspects, the system log shall be available for download as a text file, and can be viewable from the options screen. The system log can contain time-stamped records of all significant system events. The timestamp shall be independent of the user's clock setting. Examples of 'significant system events' are: Maintenance start/stop times; System Errors; Start/Stop Measurement Mode; User Data Downloads; Options Changes by User; and Power-ups.

The MC 300 of the ammonia sensor 20 is configured to handle exceptions and off-normal events during its operation. These events will not cause ammonia monitoring system 10 instability, hardware damage, or an unsafe situation. Exceptions are normally handled by error messaging prompting the user to take action.

As discussed above, the ammonia sensor 20 is typically mounted in a poultry house control room 12b, adjacent to a house controller 30, which regulates ventilation, light, heating, curtains, water sprinklers, food dispensers, and other systems in the poultry holding area 12a, generally based on readings of temperature, humidity, and bird weight that the house controller 30 takes with its own sensor systems. Several controllers on the market (e.g., controllers supplied by ChoreTime Brock) already have an input for "ammonia level" built into them, but at present this input is unused. No industry standard exists as to data format for this input. Therefore, the communication connector 54 of the ammonia sensor 20 can be configured to conform to interface specifications defined by one or more of the controller vendors.

Embodiments of the ammonia sensor 20 may be designed for compatibility with the controller output interface, so that commands from the controller could potentially be received and managed. The following design "hooks" may be built into the hardware (i.e., MC 300) of the ammonia sensor 20: one or more Analog-to-Digital Converter ports going into the microprocessor; one or more dedicated SPI bidirectional interfaces; one or more dedicated 12C bidirectional interfaces; Room for signal conditioning/amplifier circuitry; and microprocessor and memory overhead to manage the above items.

Figure 15:
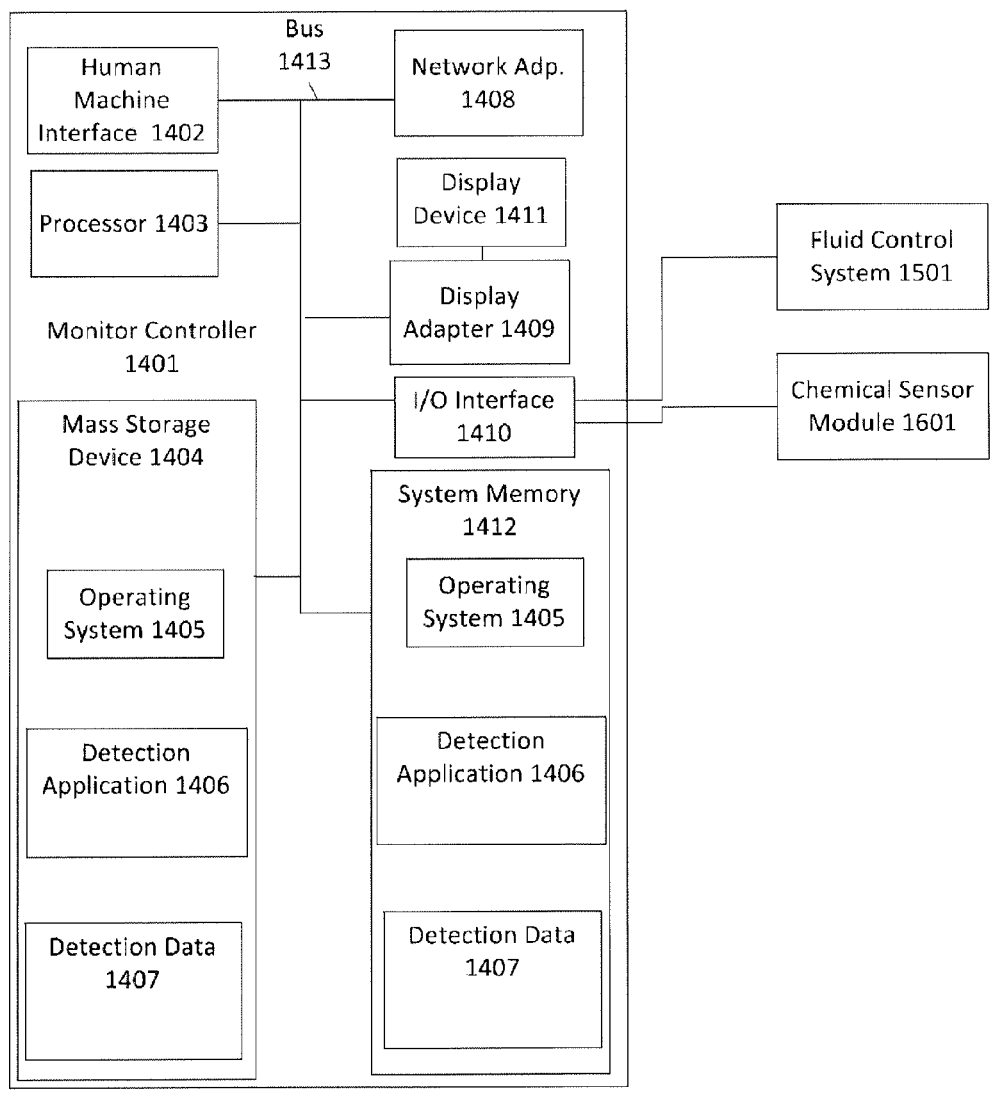
FIG. 15 is a block diagram of a monitor controller and other subsystems of an ammonia monitoring system according to an aspect.

FIG. 15 is a block diagram illustrating an exemplary operating environment for performing the disclosed methods above by the ammonia sensor 20, and more specifically the MC 300 of the ammonia sensor 20. This exemplary operating environment is only an example of an operating environment and is not intended to suggest any limitation as to the scope of use or functionality of operating environment architecture. Neither should the operating environment be interpreted as having any dependency or requirement relating to any one or combination of components illustrated in the exemplary operating environment.

The present methods and systems can be operational with numerous other general purpose or special purpose computing system environments or configurations. Examples of well-known computing systems, environments, and/or configurations that can be suitable for use with the systems and methods comprise, but are not limited to, personal computers, server computers, laptop devices, and multiprocessor systems. Additional examples comprise set top boxes, programmable consumer electronics, network PCs, minicomputers, mainframe computers, distributed computing environments that comprise any of the above systems or devices, and the like.

The processing of the disclosed methods and systems can be performed by software components. The disclosed systems and methods can be described in the general context of computer-executable instructions, such as program modules, being executed by one or more computers or other devices. Generally, program modules comprise computer code, routines, programs, objects, components, data structures, etc., that perform particular tasks or implement particular abstract data types. The disclosed methods can also be practiced in grid-based and distributed computing environments where tasks are performed by remote processing devices that are linked through a communications network. In a distributed computing environment, program modules can be located in both local and remote computer storage media including memory storage devices.

Figure 13:
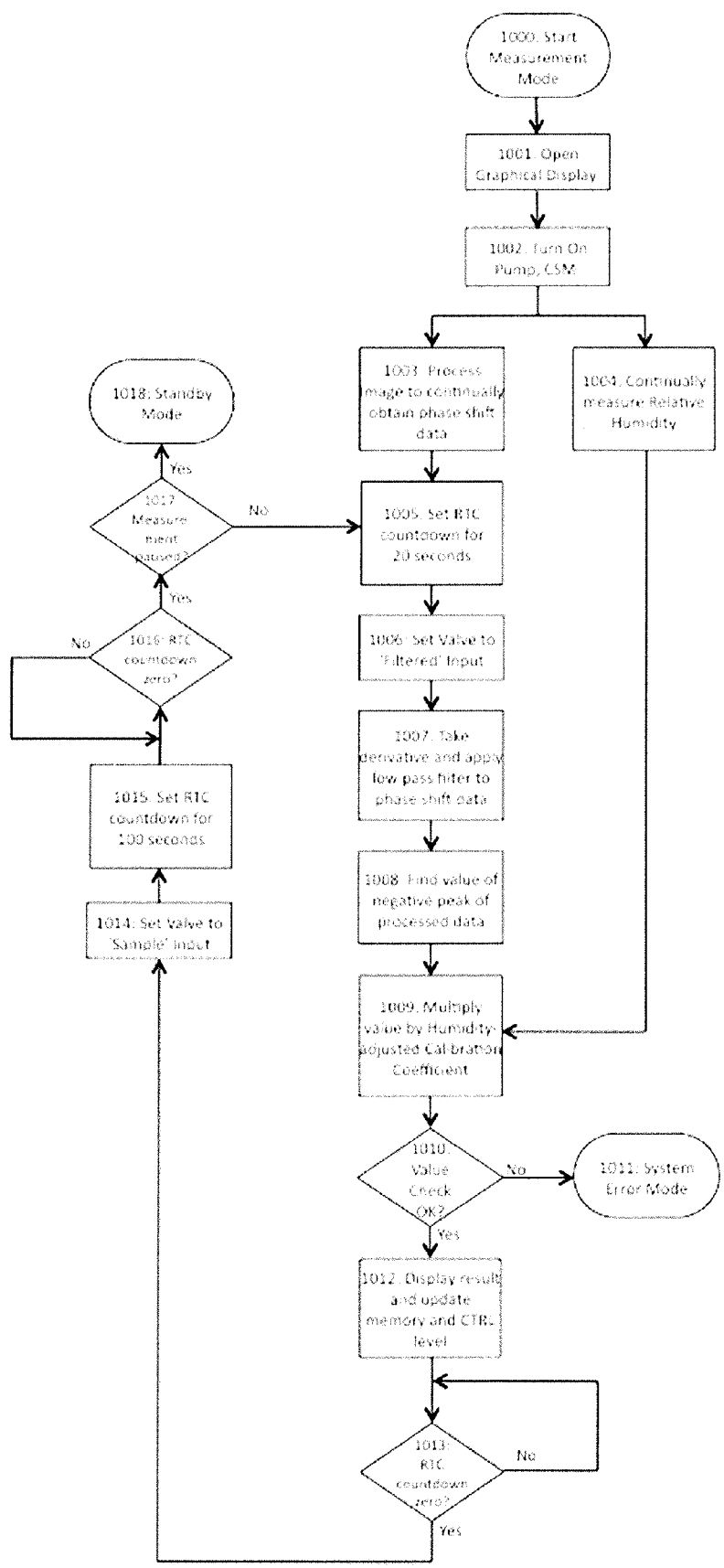
FIG. 13 is a flow diagram of a method performed by the ammonia monitoring system of FIG. 1.

Further, one skilled in the art will appreciate that the systems and methods disclosed herein can be implemented via the monitor controller (MC) 1401 illustrated in FIG. 13 (the MC 1401 can be thought of as a general-purpose computing device like a computer board 1401 but contained within the ammonia sensor 20). The components of the MC 1401 can comprise, but are not limited to, one or more processors or processing units 1403, a system memory 1412, and a system bus 1413 that couples various system components including the processor 1403 to the system memory 1412. In the case of multiple processing units 1403, the system can utilize parallel computing.

The system bus 1413 represents one or more of several possible types of bus structures, including a memory bus or memory controller, a peripheral bus, an accelerated graphics port, and a processor or local bus using any of a variety of bus architectures. By way of example, such architectures can comprise an Industry Standard Architecture (ISA) bus, a Micro Channel Architecture (MCA) bus, an Enhanced ISA (EISA) bus, a Video Electronics Standards Association (VESA) local bus, an Accelerated Graphics Port (AGP) bus, and a Peripheral Component Interconnects (PCI), a PCI-Express bus, a Personal Computer Memory Card Industry Association (PCMCIA), Universal Serial Bus (USB) and the like. The bus 1413, and all buses specified in this description can also be implemented over a wired or wireless network connection and each of the subsystems, including the processor 1403, a mass storage device 1404, an operating system 1405, detection application 1406, detection data 1407 (including the ammonia concentration amounts, thresholds, etc.), a network adapter 1408, system memory 1412, an Input/Output Interface 1410, a display adapter 1409, a display device 1411, and a human machine interface 1402.

The MC 1401 can comprise computer readable media. Exemplary readable media can be any available media that is accessible by the MC 1401 and comprises, for example and not meant to be limiting, both volatile and non-volatile media, removable and non-removable media. The system memory 1412 comprises computer readable media in the form of volatile memory, such as random access memory (RAM), and/or non-volatile memory, such as read only memory (ROM). The system memory 1412 typically contains data such as detection data 1407 and/or program modules such as operating system 1405 and detection application 1406 that are immediately accessible to and/or are presently operated on by the processing unit 1403.

In another aspect, the MC 1401 can also comprise other removable/non-removable, volatile/non-volatile computer storage media. By way of example, FIG. 13 illustrates a mass storage device 1404 which can provide non-volatile storage of computer code, computer readable instructions, data structures, program modules, and other data for the MC 1401. For example and not meant to be limiting, a mass storage device 1404 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Optionally, any number of program modules can be stored on the mass storage device 1404, including by way of example, an operating system 1405 and detection application 1406. Each of the operating system 1405 and the detection application 1406 (or some combination thereof) can comprise elements of the programming and the detection application 1406. Detection data 1407 can also be stored on the mass storage device 1404. Detection data 1407 can be stored in any of one or more databases known in the art. Examples of such databases comprise, DB2®, Microsoft® Access, Microsoft® SQL Server, Oracle®, mySQL, PostgreSQL, and the like. The databases can be centralized or distributed across multiple systems.

In another aspect, the user can enter commands and information into the ammonia sensor via the MC 1401 through the human machine interface 1402. For example, the human machine interface can take the form of the interface 40 shown in FIG. 2. However, other input devices, including, but not limited to, a keyboard, mouse, and the like, can be used. These and other input devices can be connected to the processing unit 1403 via a human machine interface 1402 that is coupled to the system bus 1413, but can be connected by other interface and bus structures, such as a parallel port, game port, an IEEE 1394 Port (also known as a Firewire port), a serial port, or a universal serial bus (USB).

In yet another aspect, a display device 1411 can also be connected to the system bus 1413 via an interface, such as a display adapter 1409. In an aspect, the display device 1411 can be the interface 40 as shown in FIG. 2. In addition to the display device 1411, other output peripheral devices can comprise components can be connected to the MC 1401 via Input/Output Interface 1410 (e.g, the external connectors 50 of FIG. 2). Any step and/or result of the methods can be output in any form to an output device. Such output can be any form of visual representation, including, but not limited to, textual, graphical, animation, audio, tactile, and the like.

As discussed above, the MC 1401 can operate and control a fluid control system (FCS) 1501 and a chemical sensor module (CSM) 1601. The MC 1401 can be connected to the FCS 1501 and CSM 1601 through various input/output interfaces 1410.

For purposes of illustration, application programs and other executable program components such as the operating system 1405 are illustrated herein as discrete blocks, although it is recognized that such programs and components reside at various times in different storage components of the MC 1401, and are executed by the data processor(s) of the MC 1401. An implementation of the detection application 1406 can be stored on or transmitted across some form of computer readable media. Any of the disclosed methods can be performed by computer readable instructions embodied on computer readable media. The methods and systems can employ Artificial Intelligence techniques such as machine learning and iterative learning. Examples of such techniques include, but are not limited to, expert systems, case based reasoning, Bayesian networks, behavior based AI, neural networks, fuzzy systems, evolutionary computation (e.g. genetic algorithms), swarm intelligence (e.g. ant algorithms), and hybrid intelligent systems (e.g. Expert inference rules generated through a neural network or production rules from statistical learning).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention. To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, those skilled in the art will appreciate that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:
1. An automated system for monitoring the amount of ammonia in a fluid comprising:
  a. a chemical sensor module configured to track the amount of ammonia in a representative flow of the fluid, the chemical sensor module comprising:

i. an interferometer comprising:
  A. a laser;
  B. a camera; and
  C. a waveguide, wherein the waveguide is oriented within a flow cell, wherein the waveguide comprises:
    I. a sense channel covered in an ammonia adsorptive polymer; and
    II. a reference channel covered in an a non-ammonia adsorptive polymer, wherein the laser is configured to pass light through the sense channel and the reference channel as the representative flow of the fluid passes through the flow cell and the sense channel and reference channel to create an interference pattern captured by the camera in images;
b. a fluid control system for supplying the representative flow of the fluid, the fluid control system comprising:
  i. at least one intake hose configured to intake the representative flow of the fluid;
  ii. a pump configured to pump the representative flow of the fluid;
  iii. a filtered path in communication with the at least one intake hose;
  iv. an unfiltered path in communication with the at least one intake hose; and
  iv. a valve configured to switch the representative flow of the fluid from the filtered path and the unfiltered path to provide ammonia filtered representative fluid and non-ammonia filtered representative fluid to the chemical sensor module via the flow cell; and
c. a monitor controller configured to control the fluid control system and the chemical sensor module in order to determine a concentration of ammonia in the representative flow of the fluid, the monitor controller comprising:
  i. a processor; and
  ii. system memory, wherein the processor determines the concentration of ammonia in the representative fluid by:
    A. determining an appropriate measurement zone of the images from the camera;
    B. determining an interference pattern period within the measurement zone;
    C. determining a phase shift from the interference pattern period;
    D. correlating data from the phase shift with calibration data to obtain an ammonia concentration reading; and
    E. processing the ammonia concentration reading to eliminate noise and other potential faulty data to determine the ammonia concentration reading, wherein the automated ammonia monitoring system is further configured to communicate with a control system to selectively remove ammonia from the fluid responsive to the detection of the ammonia when notified by the monitor controller that the ammonia concentration reading is above an ammonia threshold.

2. The automated ammonia monitoring system of claim 1, wherein the ammonia adsorptive polymer coating the sense channel comprises polyvinylphenol.

3. The automated ammonia monitoring system of claim 1, wherein the chemical sensor module is configured to self-calibrate.

4. The automated ammonia monitoring system of claim 1, wherein the fluid control system is further configured to regulate temperature of the representative flow of the fluid.

5. The automated ammonia monitoring system of claim 1, wherein determining the interference pattern period within the appropriate measurement zone further comprises utilizing image processing algorithms to determine the interference pattern period.

6. The automated ammonia monitoring system of claim 5, wherein utilizing image processing algorithms to determine the interference pattern period further comprises utilizing a spatial Fourier transform algorithm to generate a dominant spatial frequency of the interference pattern.

7. The automated ammonia monitoring system of claim 6, wherein determining the data from the phase shift from the interference pattern period comprises using a phase demodulation with the dominant spatial frequency to determine the data from the phase shift.

\* \* \* \* \*